United States Patent
Kumar et al.

(10) Patent No.: US 10,823,687 B2
(45) Date of Patent: Nov. 3, 2020

(54) METAL ANALYSIS DURING PHARMACEUTICAL MANUFACTURING

(71) Applicant: UHV Technologies, Inc., Fort Worth, TX (US)

(72) Inventors: Nalin Kumar, Fort Worth, TX (US); Manuel Gerardo Garcia, Jr., Lexington, KY (US)

(73) Assignee: UHV Technologies, Inc., Fort Worth, TX (US)

( * ) Notice: Subject to any disclaimer, the term of this patent is extended or adjusted under 35 U.S.C. 154(b) by 458 days.

(21) Appl. No.: 15/227,438

(22) Filed: Aug. 3, 2016

(65) Prior Publication Data

US 2017/0038319 A1 Feb. 9, 2017

Related U.S. Application Data

(60) Provisional application No. 62/200,404, filed on Aug. 3, 2015.

(51) Int. Cl.
*G01N 23/223* (2006.01)
*G01N 33/15* (2006.01)

(52) U.S. Cl.
CPC .......... *G01N 23/223* (2013.01); *G01N 33/15* (2013.01); *G01N 2223/076* (2013.01); *G01N 2223/652* (2013.01)

(58) Field of Classification Search
CPC .......... G01N 23/223; G01N 2223/076; G01N 2223/652; G01N 33/0045
See application file for complete search history.

(56) References Cited

U.S. PATENT DOCUMENTS

| | | | |
|---|---|---|---|
| 2,194,381 | A | 9/1937 | Cadman |
| 2,417,878 | A | 2/1944 | Luzietti et al. |
| 2,942,792 | A | 7/1957 | Anderson et al. |
| 2,953,554 | A | 9/1960 | Miller et al. |
| 3,512,638 | A | 5/1970 | Chengges et al. |
| 3,662,874 | A | 5/1972 | Muller |
| 3,791,518 | A | 2/1974 | Vanderhoof |

(Continued)

FOREIGN PATENT DOCUMENTS

| | | |
|---|---|---|
| CA | 2893877 | 12/2015 |
| CN | 200953004 | 9/2007 |

(Continued)

OTHER PUBLICATIONS

B. Shaw, "Applicability of total reflection X-ray fluorescence (TXRF) as a screening platform for pharmaceutical inorganic impurity analysis," Journal of Pharmaceutical and Biomedical Analysis, vol. 63, 2012, pp. 151-159.

(Continued)

*Primary Examiner* — Kenneth J Malkowski
(74) *Attorney, Agent, or Firm* — Kelly Kordzik; Matheson Keys & Kordzik PLLC

(57) ABSTRACT

A system and method for detecting, measuring, and analyzing for metallic impurities in pharmaceutical drugs and compounds utilizes an x-ray fluorescence system. The system and method may be co-located with a pharmaceutical manufacturing process for in-line continuous monitoring of metal impurities. The pharmaceutical products may be in a form selected from a powder, slurry, pill, tablet, and gel.

19 Claims, 13 Drawing Sheets

(56) References Cited

U.S. PATENT DOCUMENTS

| | | |
|---|---|---|
| 3,955,678 A | 5/1976 | Moyer |
| 3,973,736 A | 8/1976 | Nilsson |
| 3,974,909 A | 8/1976 | Johnson |
| 4,004,681 A | 1/1977 | Clewett et al. |
| 4,031,998 A | 6/1977 | Suzuki et al. |
| 4,044,897 A | 8/1977 | Maxted |
| 4,317,521 A | 3/1982 | Clark et al. |
| 4,413,721 A | 11/1983 | Bollier |
| 4,488,610 A | 12/1984 | Yankloski |
| 4,572,735 A | 2/1986 | Poetzschke et al. |
| 4,726,464 A | 2/1988 | Canziani |
| 4,834,870 A | 5/1989 | Osterberg et al. |
| 4,848,590 A | 7/1989 | Kelly |
| 5,054,601 A | 10/1991 | Sjogren et al. |
| 5,114,230 A | 5/1992 | Pryor |
| 5,433,311 A | 7/1995 | Bonnet |
| 5,462,172 A | 10/1995 | Kumagai et al. |
| 5,570,773 A | 11/1996 | Bonnet |
| 5,676,256 A | 10/1997 | Kumar et al. |
| 5,836,436 A | 11/1998 | Fortenbery et al. |
| 5,911,327 A | 6/1999 | Tanaka et al. |
| 6,076,653 A | 6/2000 | Bonnet |
| 6,100,487 A | 8/2000 | Schultz et al. |
| 6,148,990 A | 11/2000 | Lapeyre et al. |
| 6,266,390 B1 | 7/2001 | Sommer, Jr. et al. |
| 6,273,268 B1 | 8/2001 | Axmann |
| 6,313,422 B1 | 11/2001 | Anibas |
| 6,412,642 B2 | 7/2002 | Charles et al. |
| 6,457,859 B1 | 10/2002 | Lu et al. |
| 6,519,315 B2 | 2/2003 | Sommer, Jr. et al. |
| 6,795,179 B2 | 9/2004 | Kumar |
| 6,888,917 B2 | 5/2005 | Sommer, Jr. et al. |
| 6,983,035 B2 | 1/2006 | Price et al. |
| 7,073,651 B2 | 7/2006 | Costanzo et al. |
| 7,099,433 B2 | 8/2006 | Sommer et al. |
| 7,200,200 B2 | 4/2007 | Laurila et al. |
| 7,341,154 B2 | 3/2008 | Boer |
| 7,564,943 B2 | 7/2009 | Sommer, Jr. et al. |
| 7,616,733 B2 | 11/2009 | Sommer et al. |
| 7,674,994 B1 | 3/2010 | Valerio |
| 7,763,820 B1 | 7/2010 | Sommer, Jr. et al. |
| 7,848,484 B2 | 12/2010 | Sommer, Jr. et al. |
| 7,886,915 B2 | 2/2011 | Shulman |
| 7,903,789 B2 | 3/2011 | Morton et al. |
| 7,978,814 B2 | 7/2011 | Sommer et al. |
| 7,991,109 B2 | 8/2011 | Golenhofen |
| 8,073,099 B2 | 12/2011 | Niu et al. |
| 8,144,831 B2 | 3/2012 | Sommer, Jr. et al. |
| 8,172,069 B2 | 5/2012 | Prakasam |
| 8,476,545 B2 | 7/2013 | Sommer et al. |
| 8,553,838 B2 | 10/2013 | Sommer et al. |
| 8,567,587 B2 | 10/2013 | Faist et al. |
| 8,576,988 B2 | 11/2013 | Lewalter et al. |
| 8,654,919 B2 | 2/2014 | Sabol et al. |
| 8,855,809 B2 | 10/2014 | Spencer et al. |
| 8,903,040 B2 | 12/2014 | Maeyama et al. |
| 2003/0038064 A1 | 2/2003 | Harbeck et al. |
| 2003/0147494 A1 | 8/2003 | Sommer, Jr. et al. |
| 2006/0239401 A1 | 10/2006 | Sommer, Jr. et al. |
| 2008/0029445 A1 | 2/2008 | Russcher et al. |
| 2010/0017020 A1 | 1/2010 | Hubbard-Nelson et al. |
| 2010/0195795 A1 | 8/2010 | Golenhofen |
| 2010/0264070 A1 | 10/2010 | Sommer, Jr. et al. |
| 2010/0282646 A1 | 11/2010 | Looy et al. |
| 2012/0148018 A1 | 6/2012 | Sommer, Jr. et al. |
| 2012/0288058 A1 | 11/2012 | Maeyama et al. |
| 2013/0079918 A1* | 3/2013 | Spencer ............... B07C 5/3416 700/223 |
| 2013/0092609 A1 | 4/2013 | Andersen |
| 2013/0304254 A1 | 11/2013 | Torek et al. |

FOREIGN PATENT DOCUMENTS

| | | |
|---|---|---|
| CN | 201440132 | 4/2010 |
| CN | 201464390 | 5/2010 |
| CN | 101776620 A | 7/2010 |
| CN | 201552461 | 7/2010 |
| CN | 103745901 | 4/2014 |
| CN | 10177620 B | 6/2014 |
| CN | 203688493 | 7/2014 |
| CN | 204359695 | 5/2015 |
| CN | 204495749 | 7/2015 |
| CN | 204537711 | 8/2015 |
| CN | 204575572 | 8/2015 |
| EP | 0011892 | 11/1983 |
| EP | 0074447 | 1/1987 |
| EP | 0433828 A2 | 12/1990 |
| EP | 0351778 B1 | 10/1993 |
| JP | 5083196 | 11/2012 |
| RU | 2004101401 | 2/2005 |
| RU | 2006136756 | 4/2008 |
| RU | 2339974 | 11/2008 |
| RU | 2361194 | 7/2009 |
| WO | 2013/180922 A1 | 12/2013 |
| WO | 2015/195988 | 12/2015 |

OTHER PUBLICATIONS

Briefing Elemental Impurities—Limits, Revision Bulletin, The United States Pharmacopeial Convention, Feb. 1, 2013, 3 pages.

Chapter 6, Functional Description, S2 Picofox User Manual, 2008, pp. 45-64.

D. Bradley, "Pharmaceutical toxicity: AAS and other techniques measure pharma heavy metal," Ezine, May 15, 2011, 2 pages.

E. Margui et al., "Determiniation of metal residues in active pharmaceutical ingredients according to European current legislation by using X-ray fluorescence spectrometry," J. Anal. At. Spectrom., Jun. 16, 2009, vol. 24, pp. 1253-1257.

Elemental Impurity Analysis in Regulated Pharmaceutical Laboratories, a Primer, Agilent Technologies, Jul. 3, 2012, 43 pages.

Exova, X-ray fluorescence: a new dimension to elemental analysis, downloaded from www.exova.com on Jul. 26, 2016, 3 pages.

G. O'Neil, "Identification and Analysis of Heavy Metals in Solution (Hg, Cu, Pb, Zn, Ni) by Use of in Situ Electrochemical X-ray Fluorescence," Analytical Chemistry, Feb. 2015, 22 pages.

Guideline for Elemental Impurities, Q3D, International Conference on Harmonisation of Technical Requirements for Registration of Pharmaceuticals for Human Use, ICH Harmonised Guideline, Current Step 4 version, Dec. 16, 2014, 77 pages.

H. Rebiere et al., "Contribution of X-Ray Fluorescence Spectrometry for the Analysis of Falsified Products," ANSM, The French National Agency for Medicines and Health Products Safety, Laboratory Controls Division, France 1 page, (date unknown).

International Alloy Designations and Chemical Composition Limits for Wrought Aluminum and Wrought Aluminum Alloys, The Aluminum Association, Inc., revised Jan. 2015, 38 pages.

International Searching Authority, International Search Report and the Written Opinion, International Application No. PCT/US2016/42850, dated Sep. 28, 2016.

International Searching Authority, International Search Report and the Written Opinion of the International Searching Authority, International Application No. PCT/US2016/45349, dated Oct. 17, 2016.

J. McComb et al., "Rapid screening of heavy metals and trace elements in environmental samples using portable X-ray fluorescence spectrometer, a comparative study," Water Air Soil Pollut., Dec. 2014, vol. 225, No. 12, pp. 1-16.

J. Mondia, "Using X-ray fluorescence to measure inorganics in biopharmaceutical raw materials," Anal. Methods, Mar. 18, 2015, vol. 7, pp. 3545-3550.

L. Goncalves, "Assessment of metal elements in final drug products by wavelength dispersive X-ray fluorescence spectrometry," Anal. Methods, May 19, 2011, vol. 3, pp. 1468-1470.

L. Hutton, "Electrochemical X-ray Fluorescence Spectroscopy for Trace Heavy Metal Analysis: Enhancing X-ray Fluorescence Detec-

(56) References Cited

OTHER PUBLICATIONS tion Capabilities by Four Orders of Magnitude," Analytical Chemistry, Apr. 4, 2014, vol. 86, pp. 4566-4572.
L. Moens et al., Chapter 4, X-Ray Fluorescence, Modern Analytical Methods in Art and Archaeology, Chemical Analysis Series, vol. 155, pp. 55-79, copyright 2000.
M. Baudelet et al., "The first years of laser-induced breakdown spectroscopy," J. Anal. At. Spectrom., Mar. 27, 2013, 6 pages.
P. R. Schwoebel et al., "Studies of a prototype linear stationary x-ray source for tomosynthesis imaging," Phys. Med Biol. 59, pp. 2393-2413, Apr. 17, 2014.
R. Sitko et al., "Quantification in X-Ray Fluorescence Spectrometry," X-Ray Spectroscopy, Dr. Shatendra K Sharma (Ed.), ISBN: 978-953-307-967-7, InTech, 2012, pp. 137-163; Available from: http://www.intechopen.com/books/x-ray-spectroscopy/quantification-in-x-ray-fluorescence-spectrometry.
Scrap Specifications Circular, Institute of Scrap Recycling Industries, Inc., effective Jan. 21, 2016, 58 pages.
T. Miller et al., "Elemental Imaging for Pharmaceutical Tablet Formulations Analysis by Micro X-Ray Fluorescence," International Centre for Diffraction Data, 2005, Advances in X-ray Analysis, vol. 48, pp. 274-283.
T. Moriyama, "Pharmaceutical Analysis (5), Analysis of trace impurities in pharmaceutical products using polarized EDXRF spectrometer NEX CG," Rigaku Journal, vol. 29, No. 2, 2013, pp. 19-21.
U.S. Appl. No. 15/213,129, filed Jul. 18, 2016.
The International Bureau of WIPO, International Preliminary Report on Patentability, International Application No. PCT/US2016/045349, dated Feb. 15, 2018.
The International Bureau of WIPO, International Preliminary Report on Patentability, International Application No. PCT/US2016/42850, dated Jan. 25, 2018.

\* cited by examiner

METAL ANALYSIS DURING PHARMACEUTICAL MANUFACTURING

This patent application claims priority to U.S. provisional patent application Ser. No. 62/200,404, which is hereby incorporated by reference herein.

GOVERNMENT LICENSE RIGHTS

This invention was made with U.S. government support under SBIR Contract No. HHSN271201500035C awarded by the U.S. National Institutes of Health-NCATS. The U.S. government may have certain rights in this invention.

TECHNICAL FIELD

The present invention relates in general to pharmaceutical manufacturing, and in particular, to the analysis of metal impurities during the manufacturing of pharmaceutical drugs and compounds.

BACKGROUND INFORMATION

The ability to rapidly measure metal concentrations at low ppm levels is becoming increasingly important in pharmaceutical manufacturing. And, there is a desire to develop low cost instruments that can be used for real-time online detection and analysis during manufacturing of pharmaceutical drugs and compounds. In general, there are three primary methods of incorporation of metallic impurities in such products during manufacturing:

(i) Metallic Catalysts: Metallic catalysts are extensively used during manufacturing of pharmaceutical drugs and compounds. These include metals such as palladium, rhodium, and iridium, which must be removed after the steps involving catalysis to avoid incorporation of these metals into the final products.

(ii) Production Equipment: Another source of impurities is the metal particles and broken pieces (e.g., broken sieves, etc.) from the production equipment, such as reactors, tanks, filters, and pipes. These metals can include iron (Fe), copper (Cu), and zinc (Zn), in addition to stainless steel (made of Fe, Cr, and Ni) and platinum.

(iii) Raw Materials and Excipients: Metal impurities can come from the raw materials (plants, animal proteins, rDNA, etc.) and excipients (stabilizers, fillers, binders, release agents, flavors, colors, coatings, etc.).

Ensuring the removal or reduction of these metal impurities is required to avoid toxicity associated with heavy metals.

Current metal analysis technologies include inductively coupled plasma mass spectrometry ("ICPMS") and atomic absorption spectroscopy ("AAS"), and have been used with the typical USP<232/233> testing for metal impurities such as Ag, Hg, Cd, Pb, and As. The details of these techniques and the USP testing methods is beyond the scope of this document. However, it is important to note that these approaches rely on the use of expensive equipment that cannot be conveniently co-located with the reaction and purification equipment where metal removal is performed, thus resulting in the need to transport laboratory samples for testing, adding time and cost to the drug development process.

DETAILED DESCRIPTION

Figure 1:
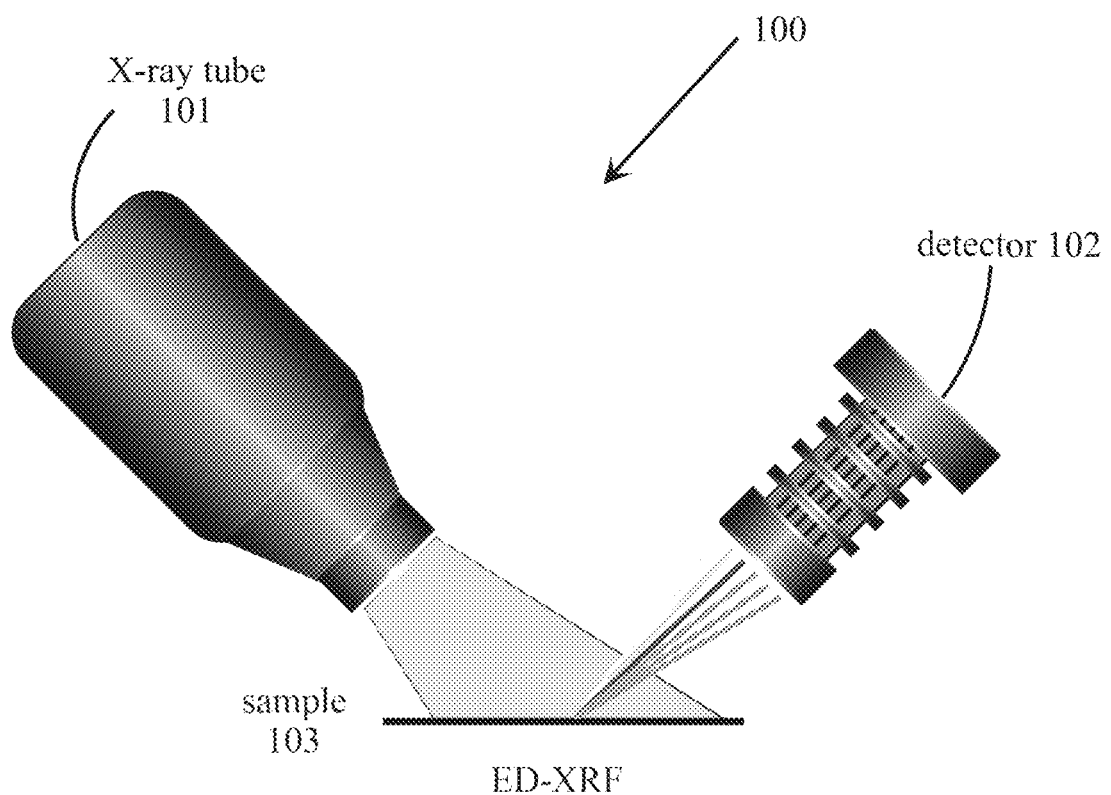
FIG. 1 illustrates an exemplary energy dispersive x-ray fluorescence ("ED-XRF") instrument for elemental analysis.

Embodiments of the present invention may be utilized for quality control, impurity testing, and manufacturing process monitoring with respect to any manufactured material, including pharmaceutical drugs and compounds, including active pharmaceutical ingredients ("APIs") and their intermediates (collectively referred to herein as "pharmaceutical products"). Embodiments of the present invention provide a system and method configured for use in a manufacturing line to continuously detect, measure, and analyze metallic impurities in a product, such as pharmaceutical products. Embodiments of the present invention allow for low ppm (parts per million) metal analysis to be performed employing affordable, robust equipment, which is easy to operate by any lab technician (i.e., not requiring specialized training). Such an instrument may be used for the continuous monitoring of metal impurities associated with continuous processing operations. Further, embodiments of the present invention provide a technique to detect, measure, and/or analyze low ppm levels of the entire suite of metals commonly used in modern synthetic organic chemistry (e.g., Pd, Rh, Cu, Zn, Fe, As, Ir, etc.), including the manufacturing of pharmaceutical products.

Additionally, embodiments of the present invention may be utilized to classify pharmaceutical products based on toxicity levels in accordance with the USP<232/233> of the United States Pharmacopoeia ("USP"), which provides the standards and details for the measurement of heavy metals in APIs and intermediates. The production of APIs and intermediates often requires the use of organometallic catalysts. Various methods are employed for the separation of the desired product from the metal complexes that still result in products that are not metal-free. The metal levels in the final product need to meet requirements for toxicity set by the USP.

As discussed herein, current analytical tools for metal analysis of pharmaceutical products are costly, require sample preparation, and are remotely located from the manufacturing production environment, including the reaction and purification equipment where metal removal is performed. In contrast, embodiments of the present invention provide systems and methods for analyzing metal content in pharmaceutical products with smaller, simpler, and cost-effective hardware located at or near the manufacturing processing stream. Metal contaminants can remain in the pharmaceutical products after wash, and it is important to detect and remove these prior to formulation. Embodiments of the present invention are configured to measure 5 ppm or less of the metal contaminant(s), can be positioned within the manufacturing production line, including the reaction and purification equipment where metal removal is performed, and provide high-speed measurement and data acquisition. While embodiments of the present invention are described herein for implementation with pharmaceutical manufacturing, embodiments of the present invention may also be utilized in the chemical and oil sectors, water and waste water systems, etc.

Within the following disclosure, embodiments of the present invention are described with respect to detecting, measuring, and analyzing samples, wherein a sample may be any material (e.g., pharmaceutical products) in which it is desired to detect, measure, and/or analyze the presence of one or more elements within the material. Within embodiments of the present invention, the pharmaceutical products may thus be referred to herein as pharmaceutical samples, or simply samples, which may be in powder, liquid, slurry, fluid, capsule, tablet, or gel form.

Embodiments of the present invention are based on proprietary XRF technology that permits the systems and methods to provide high specificity and sensitivity, with no need for sample preparation, while being able to perform the required measurements on small quantities of the samples at high speed. Furthermore, embodiments of the present invention are amenable to continuous manufacturing processes, and are modular, permitting the systems and methods to be used in various configurations.

Embodiments of the present invention may be configured for continuous measurements of trace metals in the ranges of parts per million, parts per billion, and even parts per trillion that tend to remain in the pharmaceutical products (e.g., APIs before they are formulated into the final drugs). Embodiments of the present invention are configured to be able to detect, measure, and analyze "nano-gram" quantities of a sample, either in a batch process or in-line of the manufacturing process as a continuous feed through.

As this term is used herein, "in-line" refers to a configuration whereby embodiments of the present invention are positioned somewhere within the manufacturing process, such as the manufacturing of the pharmaceutical products (e.g., APIs or their intermediate constituents), including the reaction and purification equipment where metal removal is performed. This is contrasted with prior art "off-line" technologies, which are discussed herein, which require portions of the pharmaceutical samples to be removed from the manufacturing process and sent to a remote location for the detection, measurement, and/or analysis of metal impurities within the samples. In certain embodiments of the present invention, such an in-line manufacturing process may involve the conveyance of the samples within some type of conveyer system, such as on a conveyor belt or the samples gravity fed along a ramp or chute, or even free-falling past the XRF equipment.

Requirements for any technology to be successfully implemented for real-time metal analysis in pharmaceutical manufacturing are as follows:
  (i) High Specificity: The instrument should have high specificity for metals of interest, such as Pd, Rh, Cu, Zn, Fe, As, Ir, etc., to distinguish the metals from each other.
  (ii) High Sensitivity: In addition, to make sure that all organometallics have been removed from the product, the instrument should be highly sensitive in order to detect ≤5 ppm of impurities. In fact, there are only a few analytical technologies that have this level of sensitivity, namely, ICPMS, AAS, and x-ray fluorescence ("XRF"). Some other technologies, such as electronic metal detectors based on magnetic induction, do not have the sensitivity to measure ppm levels of impurities.
  (iii) No Need for Sample Preparation: This is an important requirement for in-line real-time metal analysis in a manufacturing environment. Techniques such as ICPMS and AAS require extensive sample preparation, and require the samples to be carried to another laboratory for measurement. Thus, both ICPMS and AAS are very difficult, if not impossible, to implement for in-line real-time metal detection, measurement, and analysis. Only embodiments of the present invention implementing XRF technology as disclosed herein can perform ppm levels of measurements without any sample preparation.
  (iv) High Speed of Measurement: For in-line real-time analysis during continuous manufacturing, the metal analysis should be accomplished quickly, and the results should be available in a matter of minutes, if not seconds. Again, due to their off-line analysis requirements, both ICPMS and AAS cannot do this. It is demonstrated herein that embodiments of the present invention implementing the XRF technology disclosed herein can perform ppm levels of measurements and analysis on samples within a few seconds.
  (v) Small Size: The required instrument should be relatively small in size so that it can be conveniently co-located with the pharmaceutical reaction and purification equipment where metal removal is performed during the pharmaceutical manufacturing.
  (vi) Amenable for Continuous Manufacturing: It is desirable for the instrument to have a form factor that is amenable to be installed on a top-side of a continuous manufacturing line. At the same time, it should be amenable to a form factor (e.g., a tabletop) useful for use in batch manufacturing processes.
  (vii) Modular Design to Implement in Various Configurations: As mentioned above, the requirements as to the instrument configuration can vary significantly based on the manufacturing process (whether continuous in-line, batch, or manual/automatic). Thus, a basic modular design is desirable instead of a rigid instrument design.
  (viii) Ease of Use and Data Interpretation: For the required instrument to be useful in a manufacturing environment, it should be easy to use and interpreted by semi-skilled (i.e., non-scientist) workers.
  (ix) Power Requirements: It is desirable that the instrument can be powered with commonly available 110 VAC, and does not require any special utilities.
  (x) Low Cost: The cost of the instrument should be low as compared to ICPMS analytical instruments, which can cost more than $250K. It is believed that for a modular instrument for a manufacturing environment, a price between $25K and $50K will be desired.

XRF Technology

Figure 2:
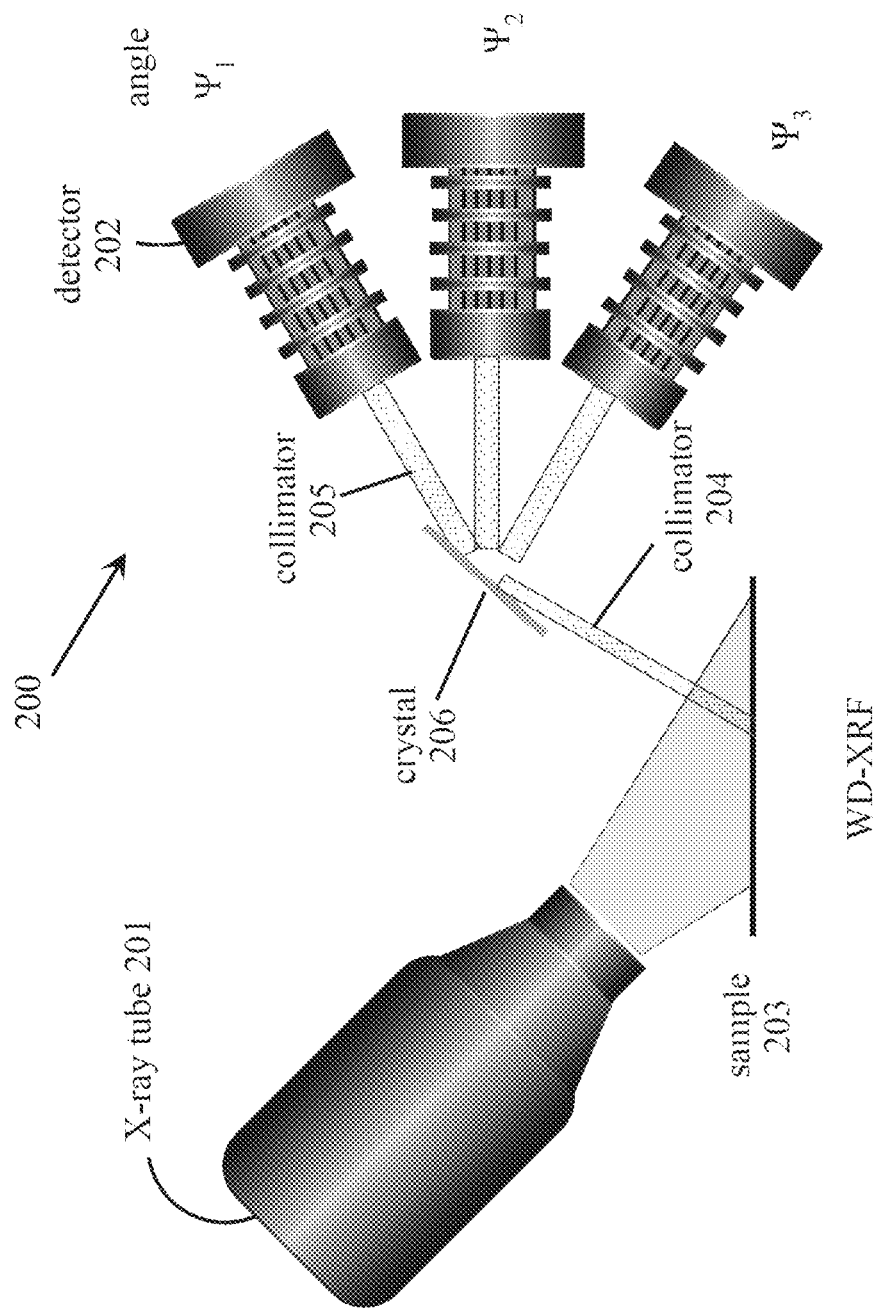
FIG. 2 illustrates an exemplary wavelength dispersive XRF ("WD-XRF") instrument for elemental analysis.
Figure 3:
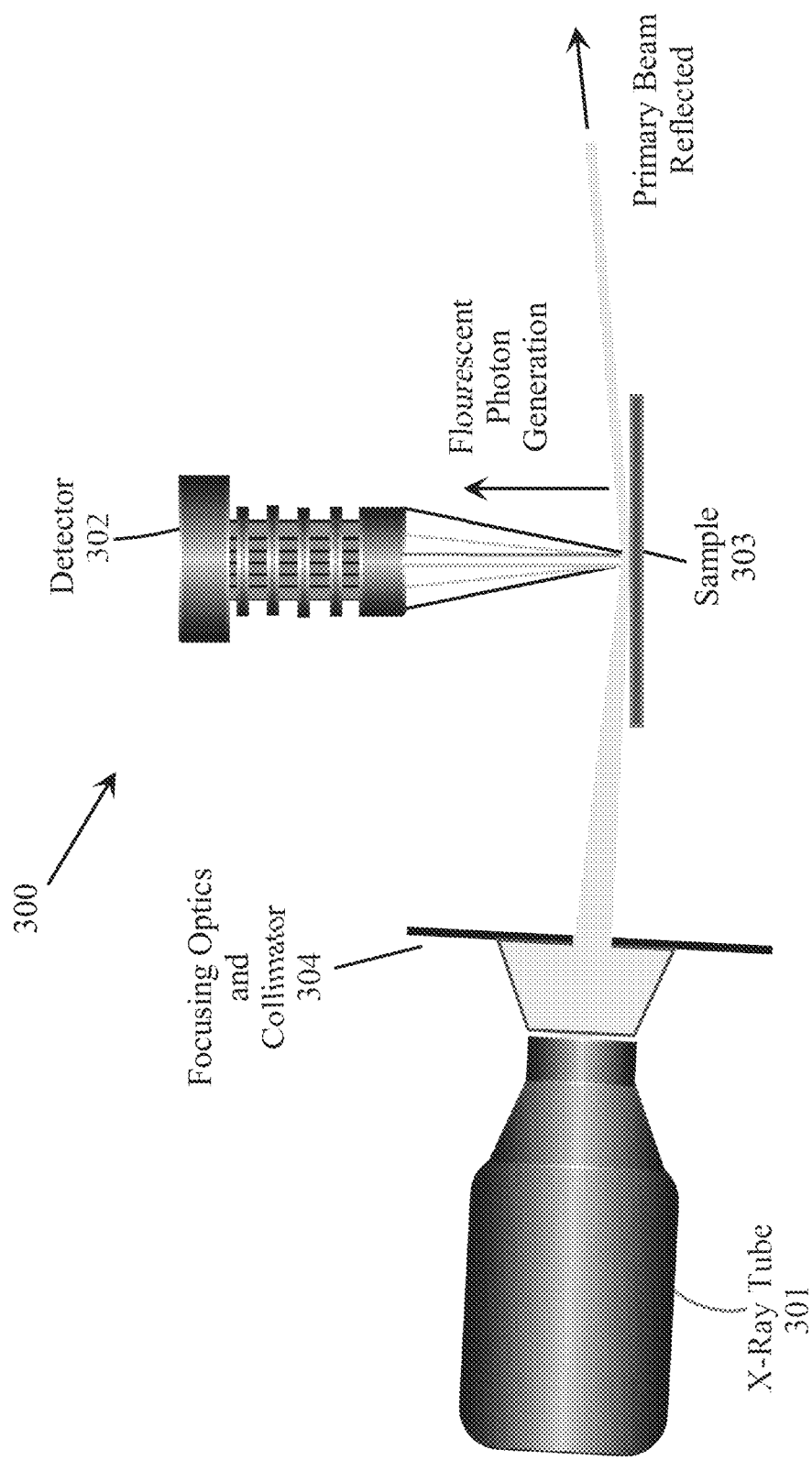
FIG. 3 illustrates an exemplary total internal x-ray fluorescence ("TXRF") instrument for elemental analysis.

FIG. 1 illustrates a schematic diagram of an exemplary energy dispersive x-ray fluorescence ("ED-XRF") system 100 for elemental analysis. FIG. 2 illustrates a schematic diagram of an exemplary wavelength dispersive XRF ("WD-XRF") system 200 for elemental analysis. FIG. 3 illustrates a schematic diagram of an exemplary total internal x-ray fluorescence ("TX RF") system 300 for elemental analysis.

Within embodiments of the present invention, the primary x-ray beam can be generated by an x-ray tube ("XRT") or a radioisotope source to cause electrons in the inner shells (of the sample) to be photo-emitted, which in turn cause higher level electrons to fall in the vacancy, resulting in the emission of fluorescent x-rays isotropically in all directions. The energy (or wavelength) of emitted fluorescent x-rays is dependent on the atomic structure of the individual atoms in the sample, and thus the elemental composition of the sample can be determined by measuring either the energy or the wavelength of emitted x-rays.

Referring again to FIG. 1, in the ED-XRF system 100, the x-ray source (e.g., tube) 101 and the x-ray detector 102 are placed at 45 degree angles with respect to the sample 103, a range of x-ray fluorescent energies are measured from the sample, and an electronic energy analyzer (not shown) is used to convert each photon energy into an electric pulse. The height of the pulse is indicative of the element, and the number of pulses per second of that height determines the relative amount of that element in the sample 103. The detector electronics can accomplish this in real-time, quickly, and automatically, giving a histogram (e.g., see the example in FIG. 4) where the x-axis (energy) represents the elements (denoted as channels), and the y-axis (counts) represents the quantifiable amount of each element present in the sample 103.

Referring again to FIG. 2, the WD-XRF system 200 has similar components as the ED-XRF system 100, but measures wavelengths of emitted x-rays instead of energy. This may be accomplished by using one or more collimators 204, 205 and a moving crystal 206. The sample 203 is irradiated by the x-ray beam from the x-ray source (e.g., tube) 201 in the same fashion. The collimator 204 directs aligned photons towards the moving crystal 206 at a specific angle. The moving crystal 206 then separates the different wavelengths of x-rays based on Bragg's Law due to the inherent atomic spacing of the crystal. The photons leaving the moving crystal 206 may be directed with collimators 205 to a plurality of detectors 202, each detector 202 dedicated to one specific wavelength, wherein each of the detectors 202 counts those photons at the specified wavelength. A WD-XRF system 200 may be utilized when looking for elements with low concentrations, or to separate elements whose XRF signal are not separable by an ED-XRF system 100. The signal resolution for the ED-XRF system 100 is approximately 140 eV compared to the WD-XRF system 200, which can resolve at 5 eV. Also, the WD-XRF system 200 is able to reduce background noise. The collimators 204, 205 and crystal 206 all function to reduce stray and unwanted background counts and noise to the detectors 202. Therefore, not only does the WD-XRF system 200 have better signal resolution qualitatively, but it also has lower limits of detection quantitatively. However, the cost for such enhanced measurements comes at the expense of power consumption. Typically, a WD-XRF system 200 uses eight times as much power as an ED-XRF system 100. Additionally, the WD-XRF system 200 is more mechanically complex and has a corresponding greater expense. And, as can be seen with the ED-XRF system 100, a small portion of the primary x-ray beam may also reach the detector 102 constituting the background, which can determine the overall signal-to-noise ratio ("SNR"), which may limit the lower limit of detection of such a configuration in the 1-20 ppm for many elements.

To improve the limit of detection ("LOD"; the smallest concentration of an element that can be detected with reasonable certainty) for such elements, a TXRF system 300, as depicted in FIG. 3, may be utilized. The configuration of a TXRF system 300 generally has less than a one-degree angle of incidence of the primary x-ray beam with respect to the sample 303, and the x-ray detector 302 is placed parallel to the sample 303. When the primary TXRF x-ray beam emitted from the x-ray source (e.g., tube) 301 (which may be directed and focused by focusing optics and a collimator 304) irradiates the sample 303 (which may include the substrate or sample holder on which the sample 303 is positioned), a combination of interference and standing waves produce a highly localized beam of x-rays on the sample 303 causing fluorescent photon generation (i.e., x-ray fluorescence). The fluorescent x-ray angular distribution has a peak intensity directly above the sample 303 where the detector 302 is located. The primary x-rays that are reflected (denoted as the Primary Beam Reflected in FIG. 3) from the sample holder pass along their reflected path and are guided away from the detector 302. Thus, separation of the reflected primary x-ray beam from the fluorescent x-rays causes a dramatic improvement in the SNR, resulting in parts per billion (ppb) to parts per trillion (ppt) measurement capability as compared to a typical ppm capability of the ED-XRF system 100 or the WD-XRF system 200. This can result in a thousand-fold improvement in sensitivity over these other XRF configurations.

Figure 7:
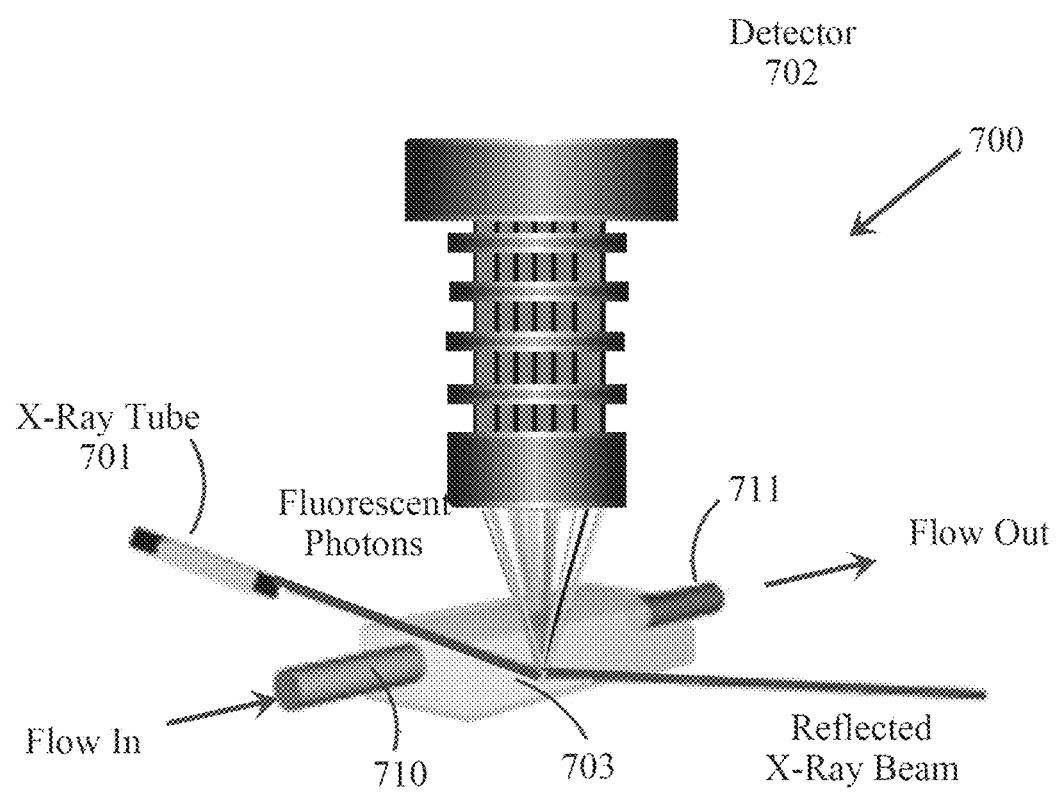
FIG. 7 illustrates a TXRF instrument configured in accordance with embodiments of the present invention for analyzing elements in a liquid.

Please note, however, that a TXRF system 300 may be sensitive to only a thin layer of the sample 303, and thus may not be suitable for uniform measurements of a sample in powder, capsule, or tablet form, but may be utilized for a thin film or the surface of a liquid sample, such as a liquid pharmaceutical product. FIG. 7 illustrates a schematic diagram of an exemplary TXRF system 700 configured in accordance with embodiments of the present invention for metal analysis of liquid pharmaceutical samples whereby a liquid pharmaceutical sample is flowed through a chamber 703 (for example, through the use of entrance and exit conduits 710, 711, respectively) for the detection of metal impurities in the liquid pharmaceutical sample. Similar to the TXRF system 300, the TXRF system 700 irradiates the liquid pharmaceutical sample by directing an x-ray beam from an x-ray source (e.g., tube) 701 into the chamber 703 whereby fluorescent photons are emitted and detected by the detector 702.

There are problems with attempting to use current XRF instruments for an in-line real-time metal analysis of pharmaceutical products. Based on the previous discussion, it is clear that XRF is a viable technology for metal analysis, and several companies, such as Bruker and Rigaku, offer commercial analytical instruments for metal analysis. However, when it comes to automated, in-line real-time XRF metal analysis, there are currently no such systems available on the market due to the following problems:

1. Cost: Cost is a primary factor for lack of widespread use of XRF technology. A handheld ED-XRF system may cost $25,000 or more, and good ones can cost twice as much. Moreover, these have relatively slow operation speeds (e.g., 10-60 seconds). Tabletop ED-XRF systems are in the $100,000-150,000 range. WD-XRF systems typically cost around $250,000 due to the extreme machining precision requirements of the spectrometer, and are only used where the cost is justified by the resolution requirements. And, if the system designer has to use several of these instruments to meet the throughput goals, the system cost (not taking the reliability issues into account) is significantly too great.

2. Complexity, size, and cost of moving WD-XRF spectrometers: As discussed earlier, the moving crystal WD-XRF cannot be used where as many as 10 spectrometers need to be utilized at the same time and in an outdoor environment.

Figure 5:
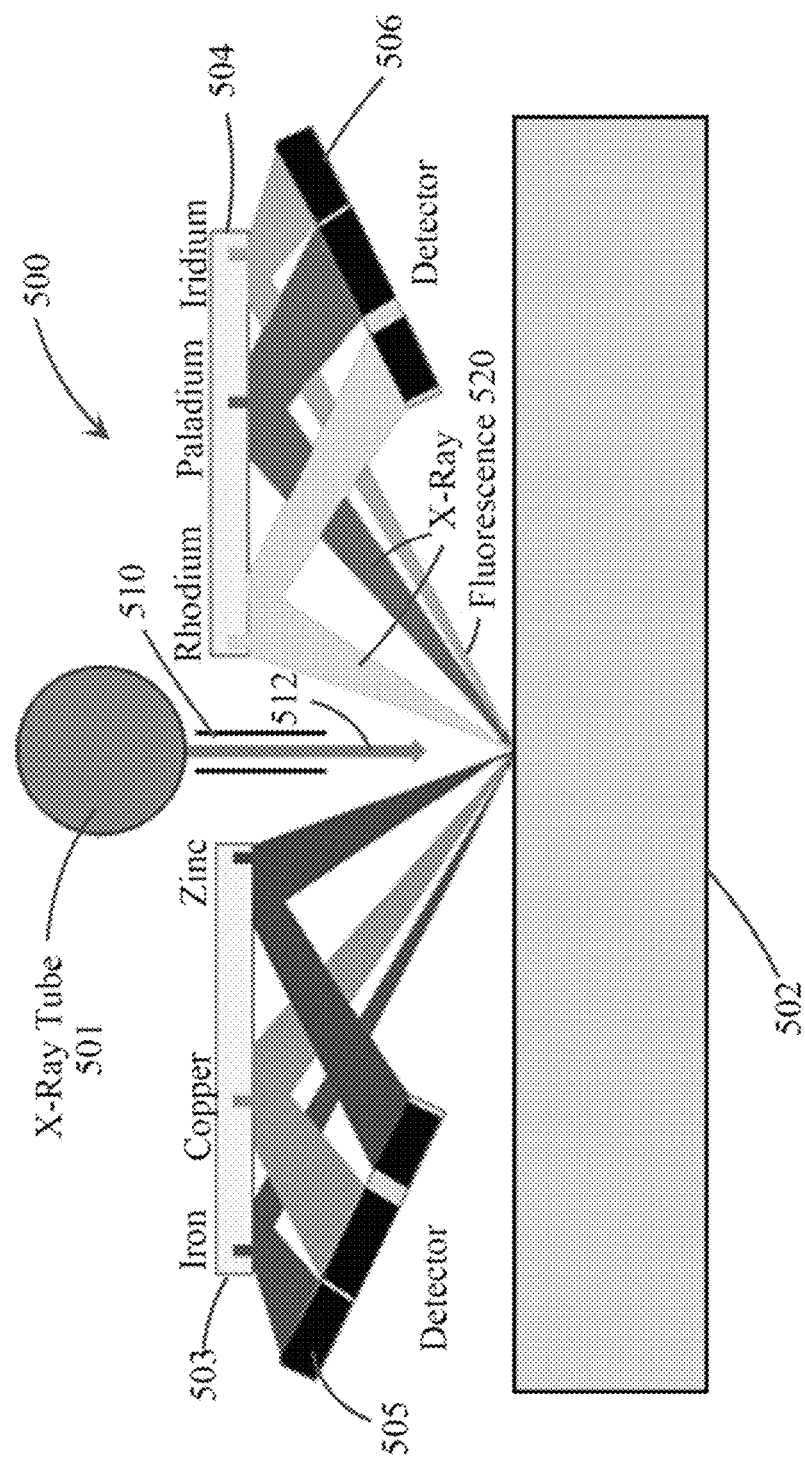
FIG. 5 illustrates a schematic diagram of an XRF module configured to detect, measure, and/or analyze a number of elements of pharmaceutical relevance.

Disclosed herein is a low cost XRF system and method for metal analysis configured in accordance with embodiments of the present invention. Referring to FIG. 5, to solve the key issues in widespread implementation of XRF technology in metal analysis, disclosed herein is an innovative variation to the WD-XRF system 200.

FIG. 5 illustrates a schematic diagram of an XRF system 500 configured to detect, measure, and/or analyze elements of pharmaceutical relevance (e.g., metallic impurities) in pharmaceutical products. No sample preparation is needed in most cases. XRF can be directly performed on pharmaceutical products in the form of loose powder, slurry, liquid, fluid, tablets, capsules, gel, etc. This technique, while capable of the desired metal analysis, does not require an expensive ED-XRF detector or moving WD-XRF detectors. At the same time, use of silicon pin diodes and low cost x-ray optics allows this module to be fabricated at very low cost, as disclosed hereinafter.

In the XRF system 500, a primary x-ray beam 512 (which may be further directed and focused by optics and/or a collimator 510) from an x-ray tube 501 irradiates the sample(s) as it passes under the x-ray tube 501 on a conveyer system (e.g., belt) 502, generating XRF photons 520 uniformly in all directions. One or more stationary x-ray optics ("XRO") mirrors or crystals 503, 504 may be strategically positioned to disperse XRF photons 520 corresponding to the various elements in the sample, which are then measured (e.g., simultaneously and continuously) in real time with detectors 505, 506.

Figure 4:
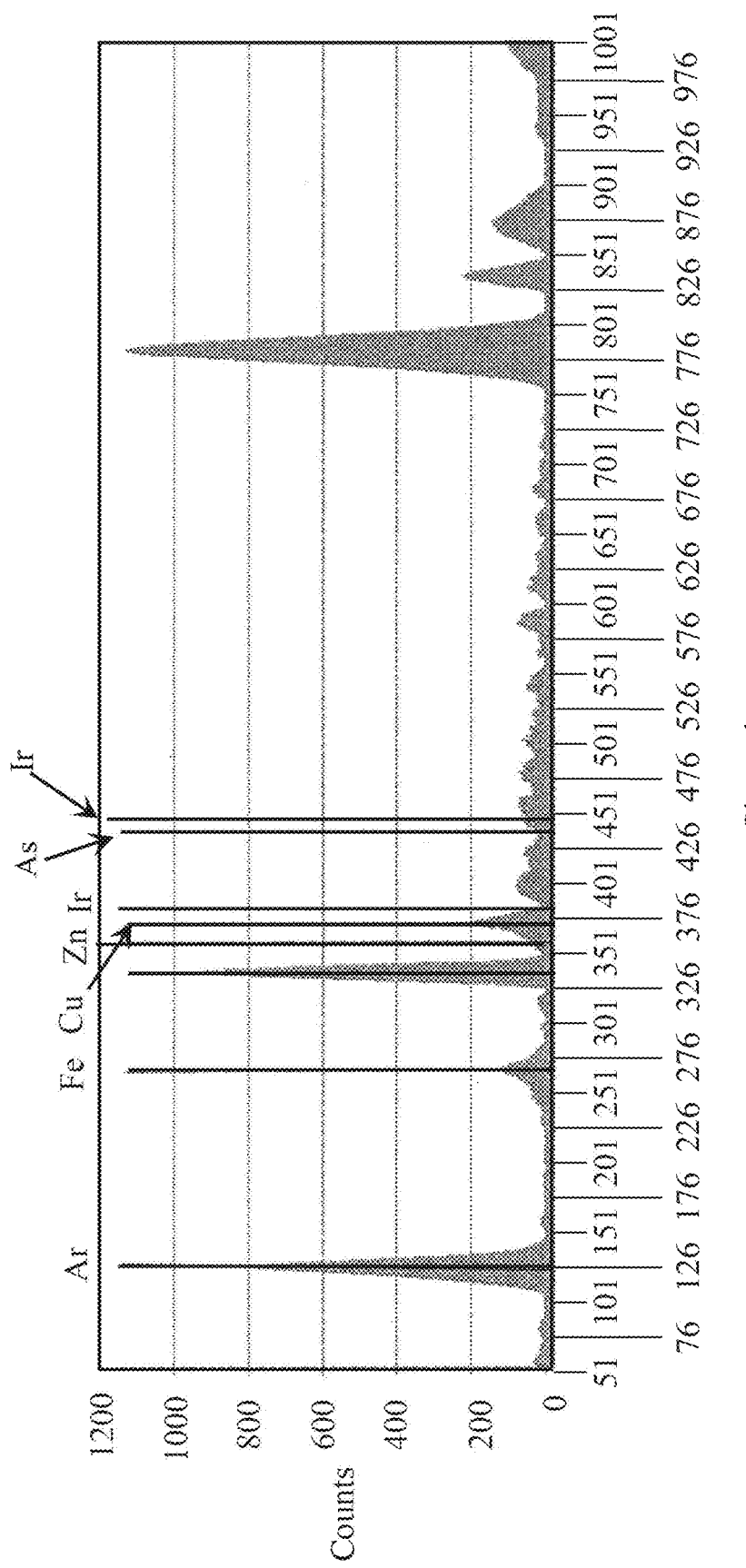
FIG. 4 illustrates an example of an energy versus counts histogram produced by embodiments of the present invention.

Since the x-ray fluorescence emissions 520 from the sample(s) is isotropic in nature, the system 500 can utilize N (N≥1) detectors to analyze multiple elements without the need for any motion or rotation of crystals and/or detectors, which is required in the WD-XRF system 200. This may be referred to herein as simultaneous XRF. Well-known collimators (not shown) may be used to assist in generating the separate XRF beam paths 520 for different metals of interest. For example, FIG. 5 shows the XRF system 500 configured to detect iron, copper, and zinc by the detector 505 while the detector 506 detects rhodium, palladium, and iridium, though embodiments of the present invention are not limited to such a configuration. The beam paths 520 are at different angles from each other, and the XROs 503, 504 that separate the wavelengths of interest for each element may be also at different angles for each element, but still obeying Bragg's Law. With the detector(s) 505, 506, XROs 503, 504, and multiple XRF beam paths 520, the elemental signals are separated, yielding a signal resolution better than 5 eV, compared to 125 eV required for a very expensive SDD (silicon drift detector). FIG. 4 shows an example of an elemental histogram produced by the XRF system 500.

The XRF system 500 may be configured similar to the one disclosed in U.S. patent application Ser. No. 15/213,129, which is hereby incorporated by reference herein.

Figure 6:
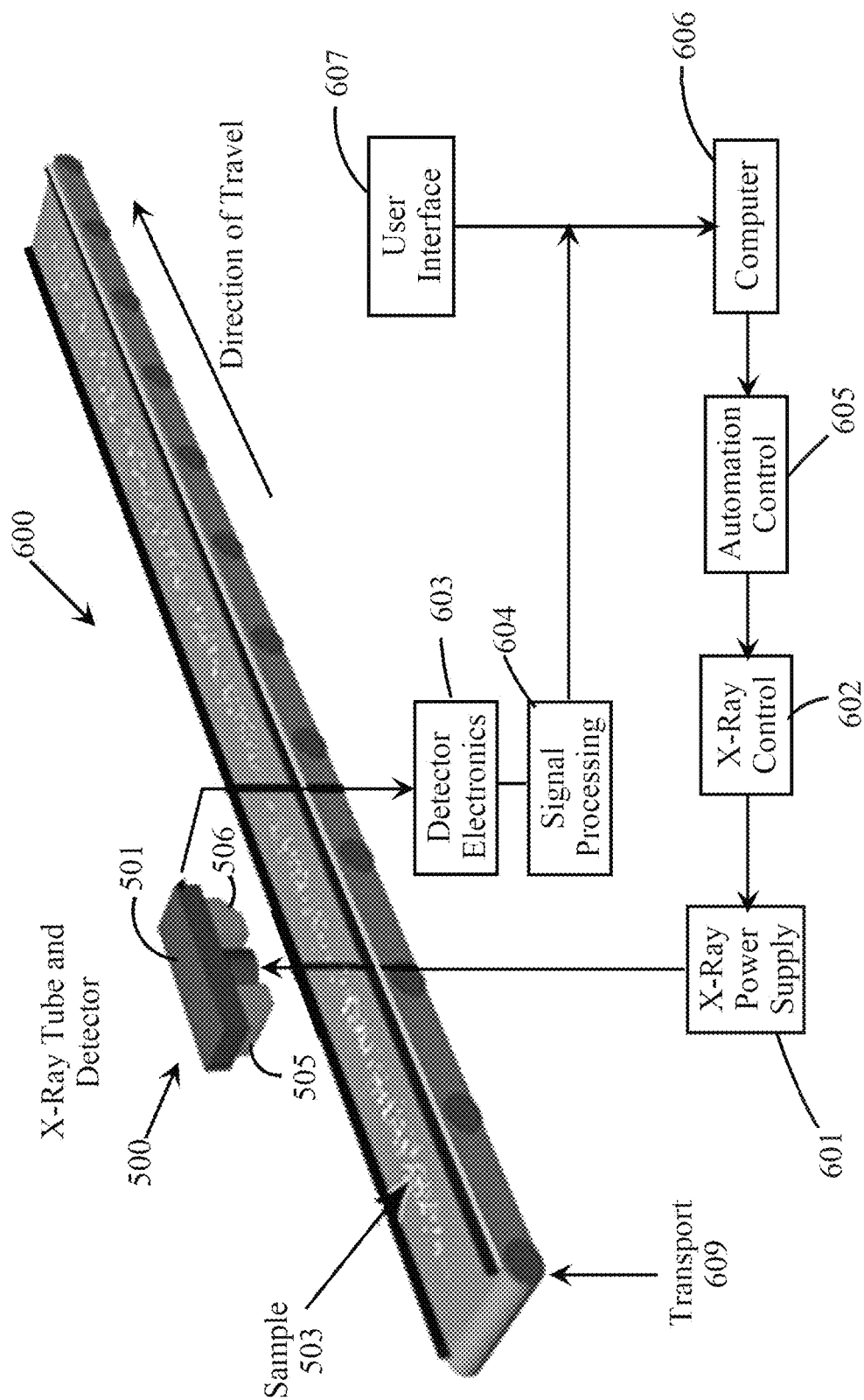
FIG. 6 illustrates a schematic diagram of a system and method configured in accordance with embodiments of the present invention.

FIG. 6 illustrates a schematic diagram of a system and method 600 configured in accordance with embodiments of the present invention in which the XRF system 500 is positioned over a conveyor or transport system (e.g., a conveyor belt) 609 carrying samples for continuous real-time metal analysis.

In embodiments of the present invention, the x-ray source 501, which may be configured as an x-ray tube, may be implemented using any well-known x-ray tube configured to irradiate samples with a required x-ray beam energy intensity. For example, the x-ray tube 501 may be a commercially available x-ray tube such as those available from Varian, including model numbers OEG-76H, EG-60, and VF-50. Alternatively, the x-ray tube 501 may be a linear x-ray tube as described herein with respect to FIGS. 9-13, which is also disclosed in U.S. patent application Ser. No. 15/213,129, which is hereby incorporated by reference herein.

Within the system and method 600 schematically illustrated in FIG. 6, one or more samples of materials (e.g., a pharmaceutical sample) may be transported along a conveyer system 502 past the XRF system 500 for detection, measurement, and/or analysis of elements (e.g., metallic impurities) within the one or more samples. As previously described, the conveyer system 502 may be co-located with the product manufacturing process, such as the manufacturing of pharmaceutical products (e.g., APIs or their intermediate constituents), including the reaction and purification equipment where metal removal is performed, including being physically positioned along an existing conveyer system utilized within such a manufacturing/processing system (such reaction and purification equipment is not shown in FIG. 6 for the sake of simplicity).

The block diagram of FIG. 6 shows the various electronics, control, and data acquisition modules, which may be utilized to operate the system and method 600, aspects of which may be implemented with well-known hardware/software. The x-ray source 501 may be powered by an x-ray power supply 601, which may be controlled by x-ray control electronics 602. Moreover, the detector electronics 603 may include well-known amplifiers for amplifying one or more of the received energy levels of the fluoresced x-rays, whereby such amplified energy levels are then processed within the signal processing module 604 before being sent to the computer system 606. Signals representing the detected XFR spectrum may be converted by the signal processing module 604 and/or the computer system 606 into a discrete energy histogram such as on a per-channel (i.e., element) basis, an example of which is shown in FIG. 4. Within embodiments of the present invention, such a signal processing module 604 and/or the computer system 606 may include a commercially available spectrum acquisition module, such as the commercially available Amptech MCA 5000 acquisition card and software programmed to operate the card. Within embodiments of the present invention, the transport system 609 may be operated to travel at a predetermined speed (e.g., by a conveyor belt motor). This predetermined speed may be programmable and adjustable by the user in any well-known manner. Within embodiments of the present invention, control/monitoring of the transport system 609 may be performed by an automation control system 605, which may also control the operation/activation of the x-ray source 501, for example, in conjunction with the monitoring of the samples travelling along the transport system 609. Such an automation control system 605 may be operated under the control of the computer system 606, or the functions for performing the automation control may be implemented in software within the computer system 606.

Within embodiments of the present invention, the x-ray tube 501 has an operating voltage of about 50 KV and a measurement time of about 30-60 seconds of a pharmaceutical sample on the transport system 609 in order to achieve a LOD of less or equal to 5 ppm.

In exemplary embodiments of the present invention, the system and method 600 may be utilized by a pharmaceutical manufacturer to determine if a particular pharmaceutical sample or batch of samples possesses an undesirable amount of a metallic impurity (or a plurality of metallic impurities). The pharmaceutical manufacturer can then determine whether to discard the sample or batch of samples, or whether the sample or batch of samples need to be further processed (e.g., cleaned/purified) to remove the undesirable metallic impurity, whereby the sample or samples may then be run through the system and method 600 again for further analysis. Furthermore, the pharmaceutical manufacturer can also utilize the measurements of the metallic impurity within the sample or samples to determine what type of further processing is required to remove the metallic impurity, or at least reduce the level of metallic impurity below a desired threshold level. Yet still further, the pharmaceutical manufacturer may utilize the measurement of the metallic impurity to modify its manufacturing process so that future pharmaceutical samples have a level of the metallic impurity less than the desired threshold.

Within embodiments of the present invention, a sorting mechanism may also be implemented on the transport system 609 downstream from the XRF system 500 to permit any samples having an undesired level of a metallic impurity to be ejected from the transport system 609 (e.g., into a receptacle). Examples of such sorting systems are described in the previously referenced U.S. patent application Ser. No. 15/213,129. For example, tablets/capsules/pills may be ejected into such receptacles. Alternatively, in a gravity-fed conveyer system, such as with a ramp or chute or a freefall system, the tablets/capsules/pills are analyzed as they fall past the XRF system 500, for later sorting by the sorting system (not shown).

Within embodiments of the present invention, it may be necessary to utilize a different anode material in the x-ray tube in order to be able to detect, measure, and/or analyze certain elements. For example, in order to detect Rh and/or Pd, the x-ray tube may need to utilize an anode made of metal(s) with energy higher than Pd (e.g., a tungsten anode).

The system and method 600 may be operating under any suitable software program for performing the functions described herein, such as Labview, which is commercially available from National Instruments. The software may be configured to control (i) the transport system 609, (ii) the XRF system 500, and (iii) the data acquisition for various sensors and XRF detectors, metal identification and quantification, software algorithms and location correlation software.

For example, the x-ray tube control 602 may be interfaced with Labview running on the computer system 606 through a digital input and output controller 605, which may be a National Instruments controller, model no. NI-USB-6008. Feedback from the x-ray tube 501 operating conditions may be sent back to Labview where the status can be seen in real time, such as with the user interface 607 of Labview. Control with the detector's digital pulse processor (the detector electronics 603 and/or the signal processing module 604) may be also through Labview.

The system and method 600 may also be configured with software configured to perform a quantitative analysis function in order to determine the types of metallic impurities, and their relative amounts within the samples. The detector(s) 505, 506 receive counts of data and place them into bins (e.g., registers) corresponding to energy levels. This raw data may then be processed into order to yield meaningful results. An exemplary algorithm begins first with obtaining the raw data in the form of a spectrum from the digital pulse (signal) processor 604. This data can be gathered instantaneously and in real time for real time spectrum processing. Second, a square root of the data is taken in order to minimize the magnitude of integer values before calculations are performed. Third, the raw data is very coarse, and the peaks may not be completely filled in due to Gaussian-like distribution that is formed from the physical counts present in the peak. Therefore, the peaks may be smoothed using a Savitsky-Golay filter. Fourth, each spectrum is present with background counts that are generated from inelastic collisions from the primary beam. This background although present underneath the peak in question, is not part of the physical counts that arise from the element that is being measured. Therefore, this background is accounted for and removed in an accurate fashion. This method is called Peak Stripping. Fifth, the calculated background is removed from the smoothed spectrum. Sixth, the data is squared to return the integer values back to their original value. Finally, the peak centers and edges are determined using a derivative function in order to locate the exact locations for start middle and end of the peak being measured. The foregoing algorithm is also disclosed in the previously referenced U.S. patent application Ser. No. 15/213,129.

As a result, embodiments of the present invention are configured to detect, measure, and analyze for metals (e.g., metallic impurities) within materials, such as pharmaceutical products.

In particular, embodiments of the present invention (such as the system and method 600) can achieve the following:

(i) Metal Impurities Detected: At least Pd, Rh, Cu, Zn, Fe, As, Ir, etc.

(ii) Selectivity: Any one of the above in (i) in the presence of any others (iii) Sensitivity: ≤5 ppm (iv) Measurement Time: ≤1 sec (v) Sampling Rate: ≥1 Hz (vi) Data Acquisition: Real-time data transfer through a USB port (vii) In-line Conveyor Speed (the transport system 609): ≥10 ft./min.

Referring to FIGS. 9-13, embodiments of the present invention may be configured to utilize a novel in-line x-ray fluorescence ("IL-XRF") system, such as for the XRF system 500. Such an IL-XRF system utilizes a novel linear x-ray tube 900, which may be configured with N (N≥1) separate x-ray sources, wherein the linear x-ray tube 900 is configured so that each of the N x-ray sources separately irradiates samples travelling along one or more singulated streams on a transport system. For example, referring to FIG. 6, if the linear x-ray tube 900 was utilized in the XRF system 500, it could be configured and positioned over the conveyor belt 609 so that the x-ray source 910 would irradiate samples travelling in one or more parallel streams so that multiple parallel streams of samples could be analyzed for metallic impurities. Though the linear x-ray tube 900 is described herein having four x-ray sources, such a linear x-ray tube may be configured with any number N (N≥1) of such x-ray sources. Furthermore, the linear x-ray tube 900 may be configured so that any of its separate x-ray sources irradiates samples travelling in multiple parallel streams. Such an IL-XRF system provides a linear x-ray tube having multiple sources instead of one each operable at a relatively low power, which significantly reduces the cost and power requirements versus having to utilize multiple separately powered x-ray sources.

Referring to FIGS. 9-12, a linear x-ray tube 900 includes an anode assembly 960, N cathode materials 990, and a grid assembly 939, positioned inside of a vacuum package 901.

The anode assembly 960 may be composed of a conductive (e.g., copper) bar mechanically attached to a high voltage feed-through 921. This bar may substantially span a length of the x-ray tube 901. Alternatively, the anode assembly 960 may be a plurality (e.g., N) of separate conductive bars connected in series. Several different coatings may be added to the copper bar 960, including rhodium, molybdenum, tungsten, silver, or any metal. This metal or combinations of metals can then be brazed onto the copper bar 960 in order to provide a layer that will generate the desired x-ray spectrum. Different metals will generate different output spectra from the x-ray tube. In addition to brazing, these metals may be mechanically attached to the bar 960. The bar 960 may also be composed of any metal other than copper. The high voltage feed-through 921 transfers a high voltage from the external environment (e.g., see the x-ray power supply 601) of the x-ray tube. The anode 960 and all the materials it comes into contact may be held at this high voltage (e.g., 0-50 kV).

Figure 9:
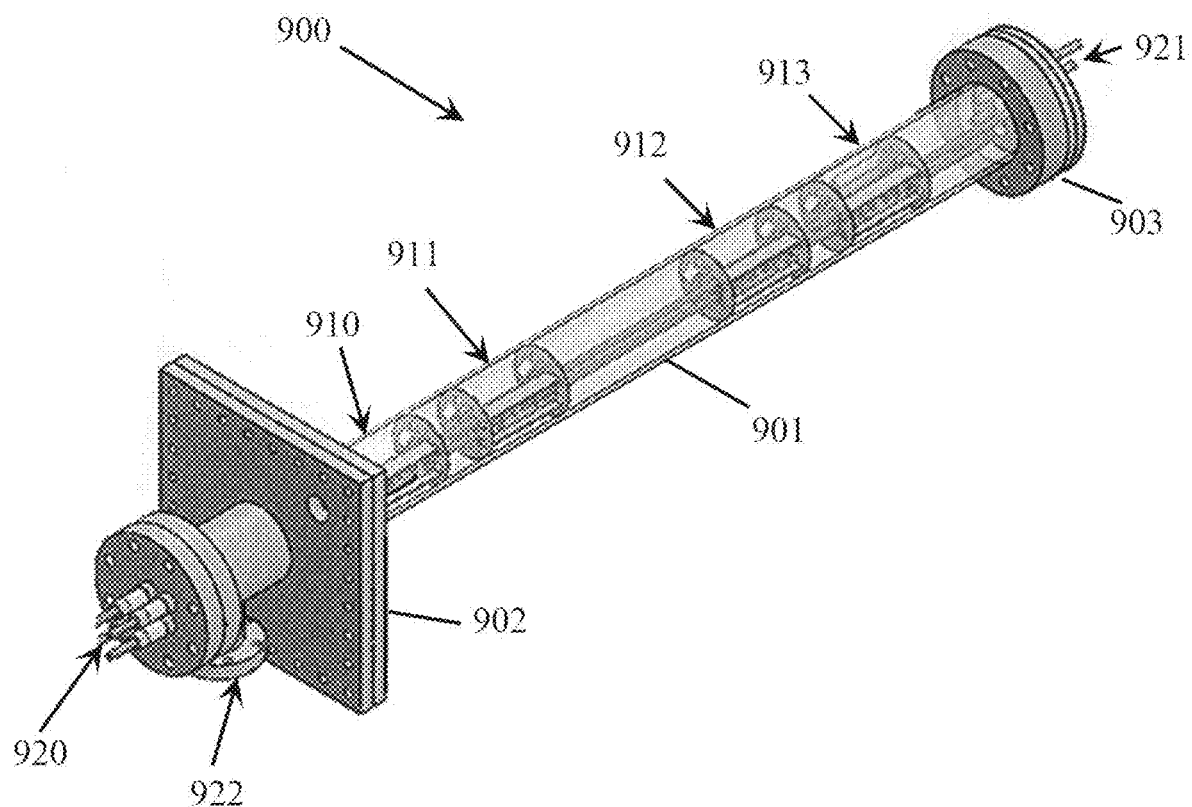
FIGS. 9, 10, 11, 12, and 13 illustrate an in-line XRF system configured in accordance with embodiments of the present invention.
Figure 10:
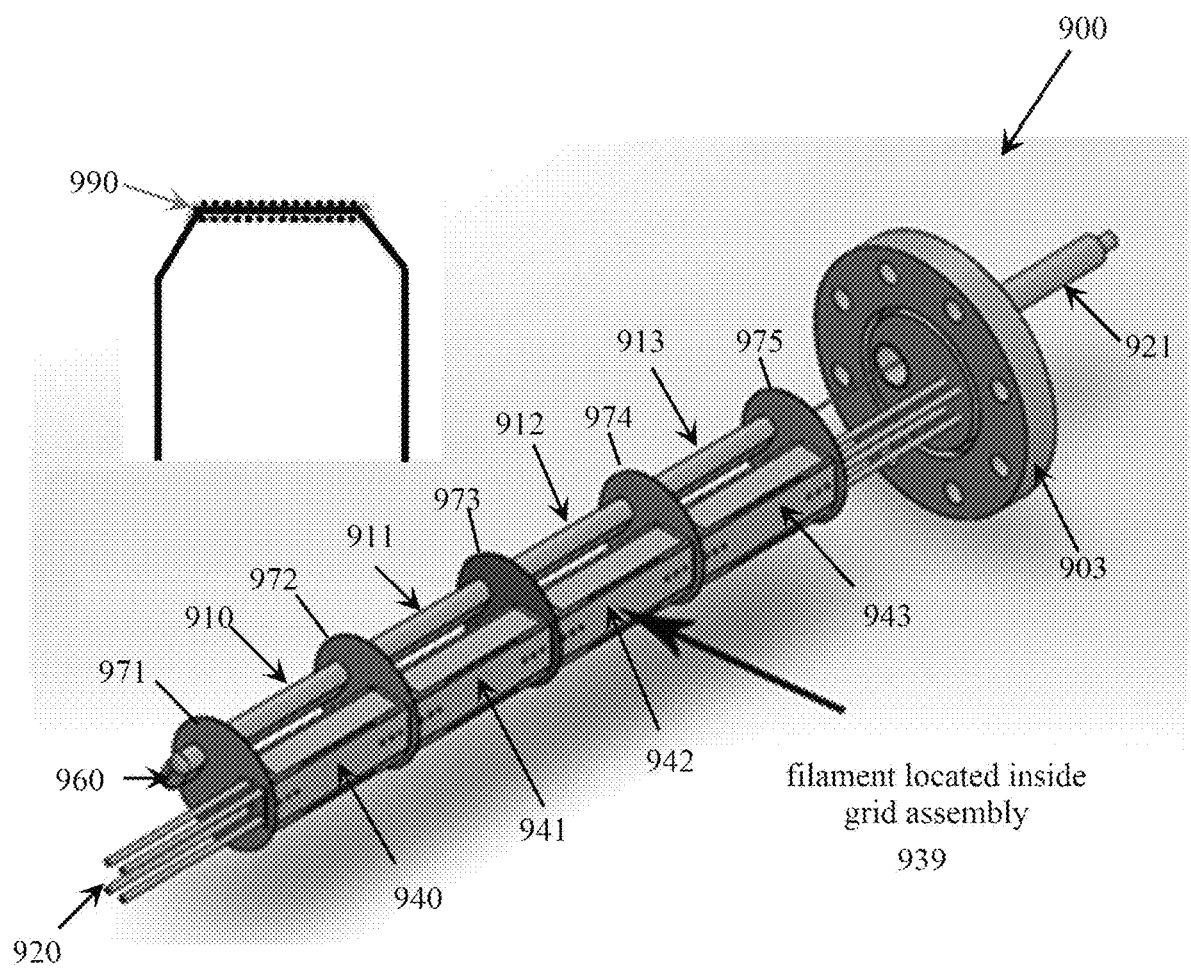

A purpose of the cathode material 990 (see inset) is to emit electrons. The cathode material 990 may be made of tungsten, but may also be thoriated tungsten, an oxide cathode, a cold cathode, or any electron emitter. The tungsten filaments may be wound into a spiral shape in order to increase the electron emission density for the volume of the spiral section of the filament shape. The two ends of the filament 990 may be held at a DC voltage, e.g., 0-15 volts with respect to ground. Application of the DC voltage causes the filaments 990 to heat to a very high temperature. When the temperature is sufficiently high, electrons are released (e-beam) from the filaments 990. A single cathode 990 produces an electron beam (e-beam) that is then focused onto a section of the anode assembly 960. The linear x-ray tube 900 may utilize an array of N (N≥1) cathodes 990 linearly arranged in order to produce multiple electron beams (e-beams), which impact the anode 960 in different sections along the length of the anode assembly 960. The cathodes may be connected to one or more feed-throughs 920 that transfer a voltage from outside the x-ray tube 900 to the filaments 990 inside the x-ray tube 900. As illustrated in FIGS. 9-10, a linear x-ray tube 900 having N x-ray sources may separately control activation and deactivation of each of the N x-ray sources by connecting each of the N cathode filaments 990 to a separate feed-through 920.

Figure 11:
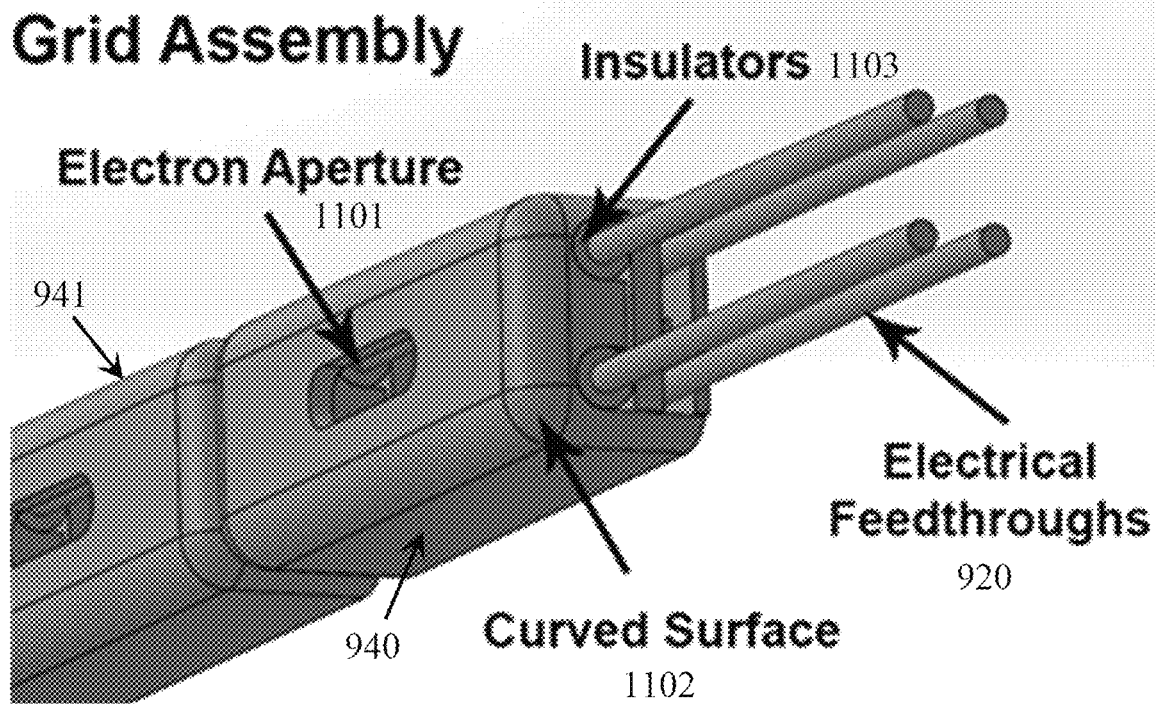
Figure 12:
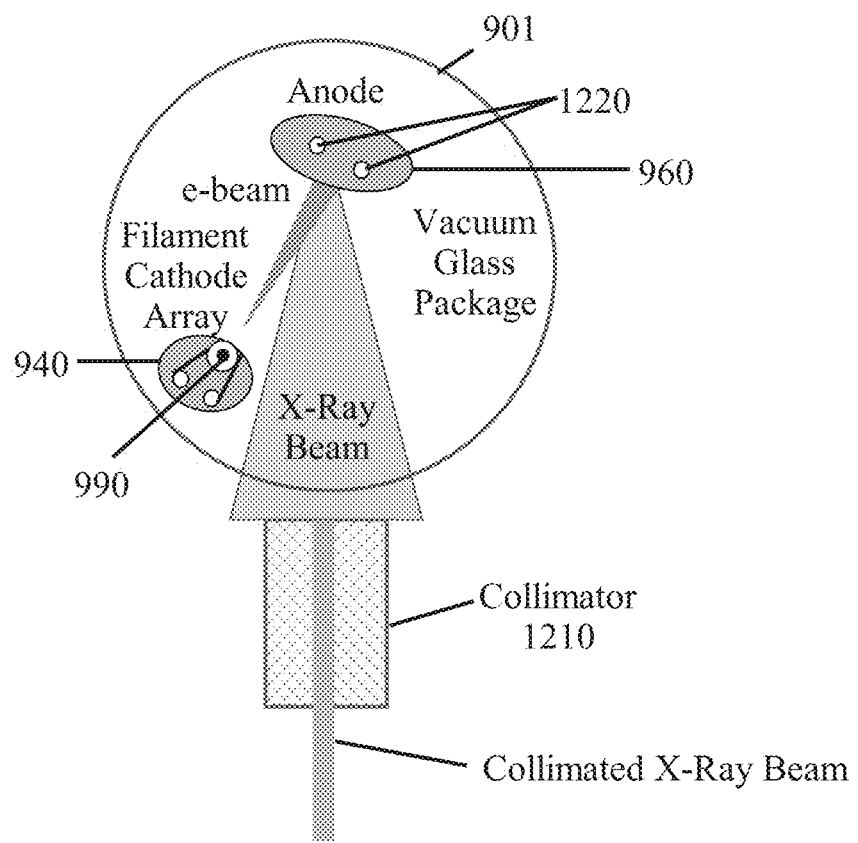

Each grid 940 . . . 943 within the grid assembly 939 may be a conductive (e.g., copper) block, which functions to isolate each of the N electron beams (e-beams) along specific paths inside the x-ray tube 900. Without the grid, electrons might scatter all around inside the x-ray tube 900 causing arcing and/or premature failure of the x-ray tube 900. The electrons that are not emitted along the intended path towards the anode 960 are collected into the grid assembly where there are electrically removed through the grid circuit. Referring to FIGS. 10-12, each of the grids 940 . . . 943 may be configured to hold a voltage used to control the flow of electrons through an aperture 1101 in the grid. Changing the voltage from a negative value to a relatively more positive value will focus the e-beam to a desired shape as the e-beam travels to the anode 960. Each grid may also be shaped to have curved surfaces, which function to generate a uniform electric field distribution in order to mitigate high voltage stress, thus helping to prevent arcs and premature failure of the x-ray tube 900. Each grid may also have a multitude of feed-throughs to allow conductive rods (e.g., copper) of differing voltages to pass through the grid assembly 939. Insulators (e.g., made of a ceramic) may be clamped to each grid to insulate these copper rods. The entire grid assembly 939 may be demountable, allowing the change of a filament 990 when it needs to be replaced.

Insulators (e.g., made of a ceramic) 971 . . . 975 may be used as high-voltage standoffs. These standoffs 971 . . . 975 may be spaced in between the grids 940 . . . 943 and in between the anode assembly 960 and cathode assembly 939. The insulators 971 . . . 975 may be utilized to mechanically hold the anode assembly 960 in place, and also serve to separate the high voltage from the low voltages. These insulators 971 . . . 975 may also have special cutouts (not shown) to increase the rate of vacuum conduction within the tube package.

A demountable vacuum package configured for implementing a linear x-ray source may include a glass tube 901, O-rings, flanges 902, 903, a gated vacuum valve 922, a turbo pump (not shown), and a rough pump (not shown). The rough pump and turbo pump pull a vacuum on the tube to a high vacuum. The long glass tube 901 holds the x-ray components. The vacuum package 901 may be demountable (e.g., by removing one of the flanges 902, 903) to allow x-ray tube components to be replaced (e.g., when they have reached their end of life). The flanges and O-rings may be used to create a reusable vacuum seal.

The linear x-ray tube 900 may include an integrated cooling system (e.g., water) (not shown). For example, water may be passed through a feed-through 1220 into the vacuum package 901 and into a cavity within the anode 960. There may be also a water feed-through (not shown) for water cooling into the grid assembly to cool the cathodes.

As shown in FIG. 12, the linear x-ray tube 901 may further include a collimator 1210 associated with each of the x-ray sources. The collimator 1210 may have an aperture that is aimed at a detection area where a particular sample is to be irradiated. As used herein, a "collimator" is a device having an aperture that limits the transmission of x-rays of an x-ray beam such that the x-rays move in the same, or nearly the same, direction. Within embodiments of the present invention, such collimators may be made from a series of closely spaced parallel metal plates utilized to direct the x-ray beam. These direct and incidental x-rays are referred to herein as background noise. Background noise may include x-rays fluoresced or reflected from objects other than the metal alloy scrap pieces, including any interior surfaces of an x-ray device chamber, the conveyor belt, or any other objects within the vicinity of the XRF system. Such background noise may be caused by the irradiating x-rays and fluoresced x-rays impacting other objects in proximity to the detector(s) and causing secondary fluorescence. Within embodiments of the present invention, the choice of resolution of an XRF spectrum may be a function of the resolution desired and the resolution capability of the one or more x-ray detectors. X-ray optics (not shown) may be used to focus a divergent primary x-ray beam into a convergent beam. X-ray optics may take the forms of crystals, capillaries, plastics, metals, or glass. The effect of the optics may reduce the amount of power needed by the x-ray tube and also increase the count rate of the spectrum as seen by the detector. Overall, this can reduce the analysis time for the XRF measurement.

Figure 13:
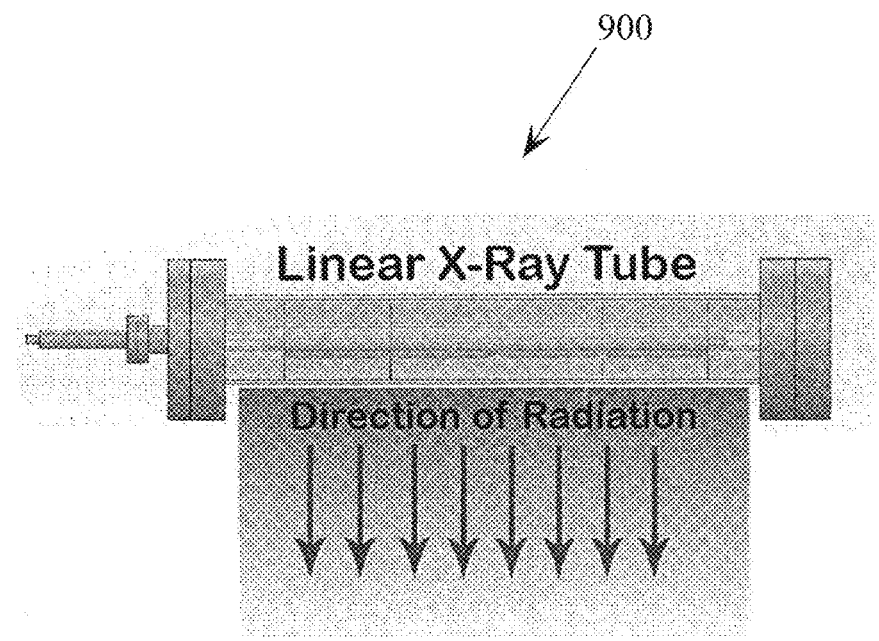

As depicted in FIG. 13, the linear x-ray tube 900 delivers a linear radiation flux outside of the tube 901, which can then be utilized to irradiate along a line generally transverse to the travelling direction of the conveyor system. Conventional x-ray sources have one spot on their anode that coincides with the electron beam size. The linear x-ray tube 900 is distinguished from a traditional x-ray source by having the ability to generate radiation in a linear and not a conical fashion. The generation of x-ray flux is dependent on this electron beam spot size. The linear x-ray tube 900 in accordance with aspects of the present disclosure has N electron beam spots arranged in a linear array, and therefore produces a directed x-ray flux with a linear component.

As has been described herein, embodiments of the present invention may be implemented to perform the various functions described for identifying, tracking, measuring, classifying, and analyzing materials, such as pharmaceutical products. Such functionalities may be implemented within hardware and/or software (such as the previously disclosed Labview), such as within one or more data processing systems (e.g., the computer system 606 of FIG. 8), such as the previously noted computer system 606 and/or automation control system 605. Nevertheless, the functionalities described herein are not to be limited for implementation into any particular hardware/software platform. As will be appreciated by one skilled in the art, aspects of the present invention may be embodied as a system, method, and/or program product. Accordingly, aspects of the present invention may take the form of an entirely hardware embodiment, an entirely software embodiment (including firmware, resident software, micro-code, etc.), or embodiments combining software and hardware aspects that may all generally be referred to herein as a "circuit," "circuitry," "module," or "system." Furthermore, aspects of the present invention may take the form of a program product embodied in one or more computer readable storage medium(s) having computer readable program code embodied thereon. (However, any combination of one or more computer readable medium(s) may be utilized. The computer readable medium may be a computer readable signal medium or a computer readable storage medium.)

A computer readable storage medium may be, for example, but not limited to, an electronic, magnetic, optical, electromagnetic, infrared, biologic, atomic, or semiconductor system, apparatus, controller, or device, or any suitable combination of the foregoing, wherein the computer readable storage medium is not a transitory signal per se. More specific examples (a non-exhaustive list) of the computer readable storage medium may include the following: an electrical connection having one or more wires, a portable computer diskette, a hard disk, a random access memory ("RAM") (e.g., RAM 820 of FIG. 8), a read-only memory ("ROM") (e.g., ROM 835 of FIG. 8), an erasable programmable read-only memory ("EPROM" or flash memory), an optical fiber, a portable compact disc read-only memory ("CD-ROM"), an optical storage device, a magnetic storage device (e.g., hard drive 831 of FIG. 8), or any suitable combination of the foregoing. In the context of this document, a computer readable storage medium may be any tangible medium that can contain or store a program for use by or in connection with an instruction execution system, apparatus, controller, or device. Program code embodied on a computer readable signal medium may be transmitted using any appropriate medium, including but not limited to wireless, wire line, optical fiber cable, RF, etc., or any suitable combination of the foregoing.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, controller, or device.

The flowchart and block diagrams in the figures illustrate architecture, functionality, and operation of possible implementations of systems, methods, processes, and program products according to various embodiments of the present invention. In this regard, each block in the flowcharts or block diagrams may represent a module, segment, or portion of code, which includes one or more executable program instructions for implementing the specified logical function(s). It should also be noted that, in some implementations, the functions noted in the blocks may occur out of the order noted in the figures. For example, two blocks shown in succession may, in fact, be executed substantially concurrently, or the blocks may sometimes be executed in the reverse order, depending upon the functionality involved.

Modules implemented in software for execution by various types of processors may, for instance, include one or more physical or logical blocks of computer instructions which may, for instance, be organized as an object, procedure, or function. Nevertheless, the executables of an identified module need not be physically located together, but may include disparate instructions stored in different locations which, when joined logically together, include the module and achieve the stated purpose for the module. Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices. The data may provide electronic signals on a system or network.

These program instructions may be provided to a processor (e.g., CPU 815 of FIG. 8) and/or controller of a general purpose computer (e.g., computer system 606), special purpose computer, or other programmable data processing apparatus (e.g., controllers 604 and/or 605) to produce a machine, such that the instructions, which execute via the processor of the computer or other programmable data processing apparatus, create means for implementing the functions/acts specified in the flowchart and/or block diagram block or blocks.

It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions. For example, a module may be implemented as a hardware circuit including custom VLSI circuits or gate arrays, off-the-shelf semiconductors such as logic chips, transistors, controllers, or other discrete components. A module may also be implemented in programmable hardware devices such as field programmable gate arrays, programmable array logic, programmable logic devices, or the like.

Computer program code, i.e., instructions, for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network ("LAN") or a wide area network ("WAN"), or the connection may be made to an external computer (for example, through the Internet using an Internet Service Provider).

These program instructions may also be stored in a computer readable storage medium that can direct a computer, other programmable data processing apparatus, controller, or other devices to function in a particular manner, such that the instructions stored in the computer readable medium produce an article of manufacture including instructions which implement the function/act specified in the flowchart and/or block diagram block or blocks.

The program instructions may also be loaded onto a computer, other programmable data processing apparatus, controller, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

One or more databases may be included in a host for storing and providing access to data for the various implementations. One skilled in the art will also appreciate that, for security reasons, any databases, systems, or components of the present invention may include any combination of databases or components at a single location or at multiple locations, wherein each database or system may include any of various suitable security features, such as firewalls, access codes, encryption, de-encryption and the like. The database may be any type of database, such as relational, hierarchical, object-oriented, and/or the like. Common database products that may be used to implement the databases include DB2 by IBM, any of the database products available from Oracle Corporation, Microsoft Access by Microsoft Corporation, or any other database product. The database may be organized in any suitable manner, including as data tables or lookup tables.

Association of certain data (e.g., for each of the metal alloy scrap pieces processed by a sorting system described herein) may be accomplished through any data association technique known and practiced in the art. For example, the association may be accomplished either manually or automatically. Automatic association techniques may include, for example, a database search, a database merge, GREP, AGREP, SQL, and/or the like. The association step may be accomplished by a database merge function, for example, using a key field in each of the manufacturer and retailer data tables. A key field partitions the database according to the high-level class of objects defined by the key field. For example, a certain class may be designated as a key field in both the first data table and the second data table, and the two data tables may then be merged on the basis of the class data in the key field. In these embodiments, the data corresponding to the key field in each of the merged data tables is preferably the same. However, data tables having similar, though not identical, data in the key fields may also be merged by using AGREP, for example.

Reference is made herein to "configuring" a device, or a device configured to perform some function. It should be understood that this may include selecting predefined logic blocks and logically associating them, such that they provide particular logic functions, which includes monitoring or control functions. It may also include programming computer software-based logic of retrofit control device, wiring discrete hardware components, or a combination of any or all of the foregoing.

In the descriptions herein, numerous specific details are provided, such as examples of programming, software modules, user selections, network transactions, database queries, database structures, hardware modules, hardware circuits, hardware chips, controllers, etc., to provide a thorough understanding of embodiments of the invention. One skilled in the relevant art will recognize, however, that the invention may be practiced without one or more of the specific details, or with other methods, components, materials, and so forth. In other instances, well-known structures, materials, or operations may be not shown or described in detail to avoid obscuring aspects of the invention.

Figure 8:
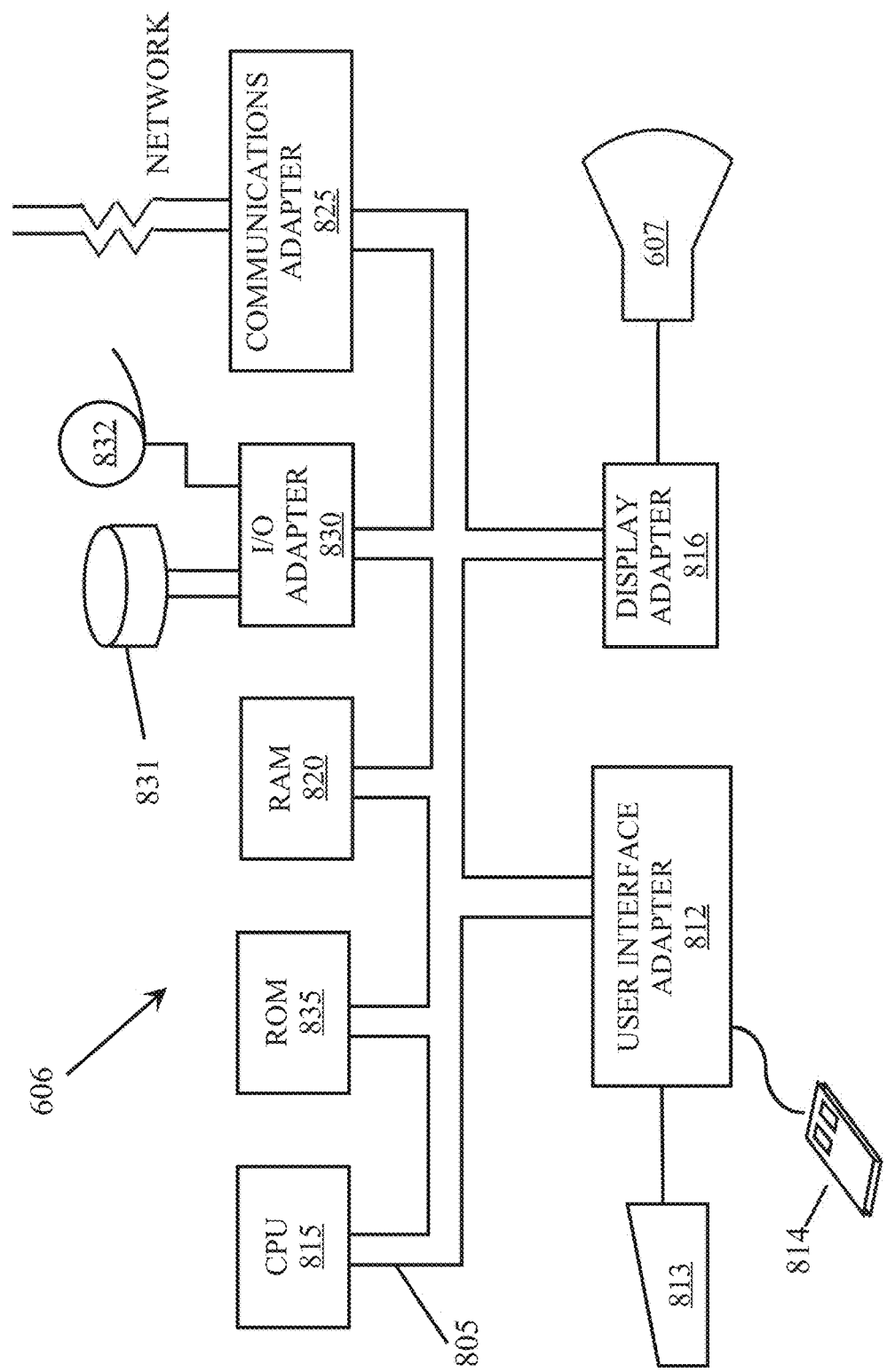
FIG. 8 illustrates a block diagram of a data processing system configured in accordance with embodiments of the present invention.

With reference now to FIG. 8, a block diagram illustrating a data processing ("computer") system 606 is depicted in which aspects of embodiments of the invention may be implemented. The computer system 606 may employ a peripheral component interconnect ("PCI") local bus architecture. Although the depicted example employs a PCI bus, other bus architectures such as Accelerated Graphics Port ("AGP") and Industry Standard Architecture ("ISA") may be used, among others. Processor ("CPU") 815, volatile memory 820, and non-volatile memory 835 may be connected to PCI local bus 805 through PCI Bridge (not shown). The PCI Bridge also may include an integrated memory controller and cache memory for processor 815. Additional connections to PCI local bus 805 may be made through direct component interconnection or through add-in boards. In the depicted example, a communication (e.g., network (LAN)) adapter 825, an I/O (e.g., small computer system interface ("SCSI") host bus) adapter 830, and expansion bus interface (not shown) may be connected to PCI local bus 805 by direct component connection. An audio adapter (not shown), a graphics adapter (not shown), and display adapter 816 (coupled to a display for displaying the user interface 607) may be connected to the PCI local bus 805 (e.g., by add-in boards inserted into expansion slots).

The user interface adapter 812 provides a connection for a keyboard 813 and a mouse 814, modem (not shown), and additional memory (not shown). The I/O adapter 830 provides a connection for a hard disk drive 831, a tape drive 832, and CD-ROM drive (not shown).

An operating system may be run on processor 815 and used to coordinate and provide control of various components within computer system 606. In FIG. 8, the operating system may be a commercially available operating system. An object oriented programming system such as Java may run in conjunction with the operating system and provide calls to the operating system from Java programs or programs executing on system 606. Instructions for the operating system, the object-oriented operating system, and programs (e.g., Labview) may be located on non-volatile memory 835 storage devices, such as a hard disk drive 831, and may be loaded into volatile memory 820 for execution by processor 815.

Those of ordinary skill in the art will appreciate that the hardware in FIG. 8 may vary depending on the implementation. Other internal hardware or peripheral devices, such as flash ROM (or equivalent nonvolatile memory) or optical disk drives and the like, may be used in addition to or in place of the hardware depicted in FIG. 8. Also, the processes of the present invention may be applied to a multiprocessor computer system.

As another example, computer system 606 may be a stand-alone system configured to be bootable without relying on some type of network communication interface, whether or not computer system 606 includes some type of network communication interface. As a further example, computer system 606 may be an embedded controller, which is configured with ROM and/or flash ROM providing non-volatile memory storing operating system files or user-generated data.

The depicted example in FIG. 8 and above-described examples are not meant to imply architectural limitations. Further, a computer program form of the present invention may reside on any computer readable storage medium (i.e., floppy disk, compact disk, hard disk, tape, ROM, RAM, etc.) used by a computer system. (The terms "computer," "system," "computer system," and "data processing system" may be used interchangeably herein.)

Reference throughout this specification to "an embodiment," "embodiments," or similar language means that a particular feature, structure, or characteristic described in connection with the embodiments is included in at least one embodiment of the present invention. Thus, appearances of the phrases "in one embodiment," "in an embodiment," "embodiments," "certain embodiments," "various embodiments," and similar language throughout this specification may, but do not necessarily, all refer to the same embodiment. Furthermore, the described features, structures, aspects, and/or characteristics of the invention may be combined in any suitable manner in one or more embodiments. Correspondingly, even if features may be initially claimed as acting in certain combinations, one or more features from a claimed combination can in some cases be excised from the combination, and the claimed combination can be directed to a sub-combination or variation of a sub-combination.

Benefits, advantages, and solutions to problems have been described above with regard to specific embodiments. However, the benefits, advantages, solutions to problems, and any element(s) that may cause any benefit, advantage, or solution to occur or become more pronounced may be not to be construed as critical, required, or essential features or elements of any or all the claims. Further, no component described herein is required for the practice of the invention unless expressly described as essential or critical.

Those skilled in the art having read this disclosure will recognize that changes and modifications may be made to the embodiments without departing from the scope of the present invention. It should be appreciated that the particular implementations shown and described herein may be illustrative of the invention and its best mode and may be not intended to otherwise limit the scope of the present invention in any way. Other variations may be within the scope of the following claims.

While this specification contains many specifics, these should not be construed as limitations on the scope of the invention or of what can be claimed, but rather as descriptions of features specific to particular implementations of the invention. Headings herein may be not intended to limit the invention, embodiments of the invention or other matter disclosed under the headings.

Herein, the term "or" may be intended to be inclusive, wherein "A or B" includes A or B and also includes both A and B. As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The terminology used herein is for the purpose of describing particular embodiments only and is not intended to be limiting of the invention. As used herein, the singular forms "a," "an," and "the" may be intended to include the plural forms as well, unless the context clearly indicates otherwise.

The corresponding structures, materials, acts, and equivalents of all means or step plus function elements in the claims below may be intended to include any structure, material, or act for performing the function in combination with other claimed elements as specifically claimed.

As used herein, "significance" or "significant" relates to a statistical analysis of the probability that there is a non-random association between two or more entities. To determine whether or not a relationship is "significant" or has "significance," statistical manipulations of the data can be performed to calculate a probability, expressed as a "p value." Those p values that fall below a user-defined cutoff point are regarded as significant. In some embodiments, a p value less than or equal to 0.05, in some embodiments less than 0.01, in some embodiments less than 0.005, and in some embodiments less than 0.001, are regarded as significant. Accordingly, a p value greater than or equal to 0.05 is considered not significant.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a defacto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of approximately 1 to approximately 4.5 should be interpreted to include not only the explicitly recited limits of 1 to approximately 4.5, but also to include individual numerals such as 2, 3, 4, and sub-ranges such as 1 to 3, 2 to 4, etc. The same principle applies to ranges reciting only one numerical value, such as "less than approximately 4.5," which should be interpreted to include all of the above-recited values and ranges. Further, such an interpretation should apply regardless of the breadth of the range or the characteristic being described.

Unless defined otherwise, all technical and scientific terms (such as acronyms used for chemical elements within the periodic table) used herein have the same meaning as commonly understood to one of ordinary skill in the art to which the presently disclosed subject matter belongs.

Although any methods, devices, and materials similar or equivalent to those described herein can be used in the practice or testing of the presently disclosed subject matter, representative methods, devices, and materials are now described.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that can vary depending upon the desired properties sought to be obtained by the presently disclosed subject matter.

As used herein, the term "about" is used to provide flexibility to a numerical range endpoint by providing that a given value may be "a little above" or "a little below" the endpoint.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

What is claimed is:

1. A system for analyzing pharmaceutical products for a presence of metallic impurities, comprising:
    a conveyer system for conveying the pharmaceutical products; and
    an x-ray fluorescence ("XRF") system positioned in proximity to the conveyor system so that an x-ray source irradiates the pharmaceutical products as they are conveyed past the XRF system, wherein the XRF system is configured to detect a presence of 5 ppm or less of a metallic element in the pharmaceutical products,
    wherein the XRF system comprises a wavelength dispersive XRF detector that includes:
        a first stationary crystal configured to separate XRF emissions from the pharmaceutical products into a first plurality of separate wavelengths each pertaining to a first plurality of different metallic elements;
        a second stationary crystal configured to separate XRF emissions from the pharmaceutical products into a second plurality of separate wavelengths each pertaining to a second plurality of different metallic elements;
        a first detector configured to detect the first plurality of different metallic elements; and
        a second detector configured to detect the second plurality of different metallic elements.

2. The system as recited in claim 1, wherein the XRF system comprises a wavelength dispersive XRF detector that includes one or more stationary crystals and one or more stationary detectors.

3. The system as recited in claim 1, wherein the metallic impurities are selected from the group consisting of palladium, rhodium, copper, zinc, iron, arsenic, and iridium.

4. The system as recited in claim 1, wherein the conveyor system conveys the pharmaceutical products past the XRF system at a speed of 10 feet per minute or greater.

5. The system as recited in claim 1, wherein the pharmaceutical products are in liquid form, wherein the conveyor system comprises a chamber through which the pharmaceutical products in liquid form flow through, wherein the chamber is positioned in proximity to the XRF system, wherein the XRF system is configured as a total internal reflection XRF system.

6. The system as recited in claim 2, wherein the pharmaceutical products are in a form selected from the group consisting of powder, slurry, pill, tablet, and gel.

7. The system as recited in claim 1, wherein the pharmaceutical products are in a form selected from the group consisting of pill, tablet, and capsule.

8. The system as recited in claim 1, wherein the x-ray source is a linear x-ray tube comprising a plurality of linearly-arranged x-ray emitters positioned within a single evacuated tube.

9. The system as recited in claim 1, wherein the conveyor system is part of a manufacturing process of the pharmaceutical products, wherein the XRF system is positioned in-line with the manufacturing process.

10. The system as recited in claim 9, wherein the manufacturing process includes purification equipment configured to remove the detected metallic element from the pharmaceutical products.

11. The system as recited in claim 1, wherein a single x-ray source irradiates the pharmaceutical products as they are conveyed past the XRF system.

12. The system as recited in claim 1, wherein the XRF system is configured so that the first detector detects the first plurality of different metallic elements simultaneously with the second detector detecting the second plurality of different metallic elements.

13. The system as recited in claim 1, wherein the metallic impurities are selected from the group consisting of rhodium, arsenic, and iridium.

14. A system for analyzing pharmaceutical products for a presence of an element, the system comprising:
    a conveyor system for conveying the pharmaceutical products along a path; and
    a wavelength dispersive x-ray fluorescence ("WD-XRF") system positioned in proximity to the conveyor system so that an x-ray source irradiates the pharmaceutical products as they are conveyed on the conveyor system, wherein the WD-XRF system is configured to detect a presence of the element in the pharmaceutical products, wherein the WD-XRF system includes one or more stationary crystals and one or more stationary detectors, wherein the one or more stationary crystals are each configured to separate XRF emissions from the pharmaceutical products into one or more separate wavelengths each pertaining to a different element, wherein the one or more stationary crystals includes:
        a first stationary crystal configured to separate XRF emissions from the pharmaceutical products into a first plurality of separate wavelengths each pertaining to a first plurality of different metallic elements; and
        a second stationary crystal configured to separate XRF emissions from the pharmaceutical products into a second plurality of separate wavelengths each pertaining to a second plurality of different metallic elements, wherein the one or more stationary detectors includes:
   a first detector configured to detect the first plurality of different metallic elements; and
   a second detector configured to detect the second plurality of different metallic elements.

15. The system as recited in claim 14, wherein the XRF system is configured so that the first detector detects the first plurality of different metallic elements simultaneously with the second detector detecting the second plurality of different metallic elements.

16. A method for analyzing pharmaceutical products for a presence of one or more metallic elements, the method comprising:
   conveying the pharmaceutical products along a path of a conveyor system;
   irradiating the pharmaceutical products with an x-ray source;
   detecting x-ray fluorescence ("XRF") emissions emanating from the irradiated pharmaceutical products; and
   analyzing the XRF emissions to determine if the pharmaceutical products contain one or more metallic elements,
   wherein the detecting of the XRF emissions further comprises:
      separating the XRF emissions into a first plurality of wavelengths using a first stationary crystal, wherein the first plurality of wavelengths each pertain to a first plurality of the one or more metallic elements;
      separating the XRF emissions into a second plurality of wavelengths using a second stationary crystal, wherein the second plurality of wavelengths each pertain to a second plurality of the one or more metallic elements;
      separately counting each of the first plurality of wavelengths using a first stationary detector; and
      separately counting each of the second plurality of wavelengths using a second stationary detector.

17. The method as recited in claim 16, further comprising conveying the pharmaceutical products along the path of the conveyor system past purification equipment configured to remove one or more of the metallic elements from the pharmaceutical products.

18. The method as recited in claim 16, wherein the pharmaceutical products are in liquid form.

19. The method as recited in claim 16, wherein the separating the XRF emissions into the first and second pluralities of wavelengths using the first and second stationary crystals is performed simultaneously.

* * * * *